(12) United States Patent
Urano et al.

(10) Patent No.: US 9,051,597 B2
(45) Date of Patent: Jun. 9, 2015

(54) FLUORESCENT SUBSTRATE FOR DETECTION OF ENZYMATIC ACTIVITY OF NITRILE-RELATED ENZYME

(71) Applicants: Mitsubishi Rayon Co., Ltd., Chiyoda-ku (JP); The University of Tokyo, Bunkyo-ku (JP)

(72) Inventors: Yasuteru Urano, Bunkyo-ku (JP); Tetsuo Nagano, Bunkyo-ku (JP); Tomoe Ohta, Bunkyo-ku (JP); Fujio Yu, Yokohama (JP)

(73) Assignees: Mitsubishi Rayon Co., Ltd., Chiyoda-ku (JP); The University of Tokyo, Bunkyo-ku (JP)

( * ) Notice: Subject to any disclaimer, the term of this patent is extended or adjusted under 35 U.S.C. 154(b) by 0 days.

(21) Appl. No.: 14/030,103

(22) Filed: Sep. 18, 2013

(65) Prior Publication Data

US 2014/0072990 A1    Mar. 13, 2014

Related U.S. Application Data

(63) Continuation-in-part of application No. 13/699,422, filed as application No. PCT/JP2011/062558 on May 25, 2011, now Pat. No. 8,697,383.

(30) Foreign Application Priority Data

May 25, 2010   (JP) ................................. 2010-119431

(51) Int. Cl.
| | | |
|---|---|---|
| *C12Q 1/34* | (2006.01) | |
| *C07D 311/82* | (2006.01) | |
| *C12Q 1/00* | (2006.01) | |
| *C12Q 1/527* | (2006.01) | |
| *C07D 311/88* | (2006.01) | |

(52) U.S. Cl.
CPC ...... *C12Q 1/527* (2013.01); *C12Q 1/34* (2013.01); *C07D 311/88* (2013.01)

(58) Field of Classification Search
CPC .............................. C07D 311/82; C12Q 1/28

USPC ................ 435/18, 195, 227, 228, 4; 549/223
See application file for complete search history.

(56) References Cited

U.S. PATENT DOCUMENTS

| | | | |
|---|---|---|---|
| 7,524,974 B2* | 4/2009 | Nagano et al. ............... 549/224 |
| 2003/0215798 A1 | 11/2003 | Short et al. | |
| 2004/0225037 A1* | 11/2004 | Lam et al. ..................... 524/90 |
| 2006/0030054 A1 | 2/2006 | Nagano et al. | |
| 2008/0014602 A1 | 1/2008 | Nagano et al. | |
| 2010/0227766 A1 | 9/2010 | Walt et al. | |

FOREIGN PATENT DOCUMENTS

| | | |
|---|---|---|
| WO | WO 98/58085 A1 | 12/1998 |
| WO | WO 2004/005917 A1 | 1/2004 |
| WO | WO 2005/024049 A1 | 3/2005 |
| WO | WO 2006/019105 A1 | 2/2006 |
| WO | WO 2008/048698 A2 | 4/2008 |

OTHER PUBLICATIONS

Urano et al. (2005). Evolution of Fluorescein as a Platform for Finely Tunable Fluorescent Probes. JACS, v127, p. 4888-4894.*
Tanaka et al. (2010). Biodegradable main-chain phosphate-caged fluorescein polymers for the evolution of enzymatic activity. Macromolecules, v43, p. 6180-6184.*
The Extended European Search Report issued Sep. 26, 2013, in Application No. / Patent No. 11786805.9-1451 / 2578694 PCT/JP2011062558.
International Search Report issued Aug. 16, 2011 in PCT/JP2011/062558.
A. Banerjee, et al., "The nitrile-degrading enzymes: current status and future prospects", Appl Microbiol Biotechnol, vol. 60, No. 1-2, 2002, pp. 33-44.
Michael S. Rappé, et al., "The Uncultured Microbial Majority", Annu. Rev. Microbiol., vol. 57, 2003, pp. 369-394.

* cited by examiner

*Primary Examiner* — Cherie M Stanfield
*Assistant Examiner* — Sean C Barron
(74) *Attorney, Agent, or Firm* — Oblon, McClelland, Maier & Neustadt, L.L.P.

(57) ABSTRACT

The object of the invention is to provide a fluorescent substrate for detecting the enzymatic activity of a nitrile-related enzyme and compound represented by formula (I) and a fluorescent substrate for detecting the enzymatic activity of a nitrile-related enzyme, which includes the compound.

17 Claims, 12 Drawing Sheets

FLUORESCENT SUBSTRATE FOR DETECTION OF ENZYMATIC ACTIVITY OF NITRILE-RELATED ENZYME

This application is a continuation-in-part of copending U.S. application Ser. No. 13/699,422 filed on Nov. 21, 2012, which is the U.S. National Phase of PCT/JP2011/062558 filed on May 25, 2011. This application claims the benefit of the filing date of Patent Application No. 2010-119431 filed in Japan on May 25, 2010. These documents are hereby expressly incorporated by reference for all purposes.

TECHNICAL FIELD

The present invention relates to a novel compound and a fluorescent substrate for detecting the enzymatic activity of a nitrile-related enzyme, which comprises the compound, as well as a method for detecting the enzymatic activity of a test substance using the above compound.

BACKGROUND ART

In the production processes for compounds serving as source materials of chemical products, enzymatic reactions are currently used due to their high conversion and selectivity, particularly due to their high stereoselectivity in the case of optically active compounds. For example, enzymatic reactions catalyzed by nitrilase, nitrile hydratase, amidase and the like are used for production of nitrile compounds (e.g., acrylamide, acrylic acid) serving as source materials of various chemical products. Nitrilase is an enzyme converting a nitrile group into a carboxylic acid group through hydrolysis, nitrile hydratase is an enzyme converting a nitrile group into an amido group through hydration, and amidase is an enzyme converting an amido group into a carboxylic acid group through hydrolysis.

Microorganisms having these enzymes have been screened from the natural environment including soil. Techniques commonly used for screening purposes involve enriching microorganisms which grow using nitrile compounds or the like as a sole nitrogen or carbon source, and selecting a microorganism having enzymatic activity from among the resulting microorganisms. For verification of enzymatic activity, a nitrile compound or an amide compound is reacted with each microorganism and the resulting product is analyzed with an instrument for high performance liquid chromatography or gas chromatography, etc.

On the other hand, there is a research report showing that microorganisms which can be isolated and cultured by currently used techniques constitute only less than 1% of the microorganisms present in the natural environment (M. S. Rappe and S. J. Giovannoni, Annu. Rev. Microbiol., 57, 369 (2003)).

For this reason, another procedure (metagenome screening) has been used in recent studies, which involves directly isolating genes (environmental DNAs or metagenomes) from the natural environment, instead of isolating microorganisms as in conventional techniques, and then screening the isolated genes to select a useful enzyme gene. The use of this procedure requires techniques for preparing a very large number of metagenome-derived recombinants and efficiently selecting active recombinants from among these recombinants. However, screening with an instrument for high performance liquid chromatography or gas chromatography is not high-throughput. Thus, there has been a demand for a novel technique which allows high-throughput screening.

Meanwhile, an invention of a fluorescent probe or fluorescent labeling agent is known as an invention directed to a fluorescent substance (WO2004/005917, WO2006/019105). However, the fluorescent substrate of the present invention useful for detection of enzymatic activity is not known.

DISCLOSURE OF THE INVENTION

The present invention has been made under these circumstances, and the problem to be solved by the present invention is to provide a novel compound and a fluorescent substrate for detecting the enzymatic activity of a nitrile-related enzyme, which comprises the compound, as well as a method for detecting the enzymatic activity of a test substance using the above compound.

As a result of extensive and intensive efforts made to solve the above problem, the inventors of the present invention have developed a compound whose fluorescence will vary by the action of a nitrile-related enzyme, e.g., a non-fluorescent (low fluorescent) substrate compound which will emit fluorescence by the action of a nitrile-related enzyme. Moreover, the inventors of the present invention have also found that the enzymatic activity of a nitrile-related enzyme can be detected in a simple manner by measuring fluorescence from the substrate of the present invention. This finding led to the completion of the present invention.

Namely, the present invention is as follows.

(1) A compound of formula (I), a salt thereof, or a hydrate thereof:

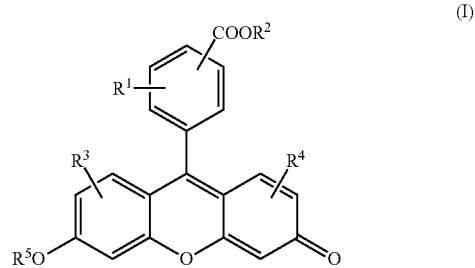

wherein $R^1$ is —CN, —CONH$_2$, —CH=CH—CN, or —CH=CH—CONH$_2$,
$R^2$ is a $C_{1-4}$ alkyl group or a halobenzyl group,
$R^3$, and $R^4$ are each independently a hydrogen atom, a halogen atom or a $C_{1-4}$ alkyl group, and
$R^5$ is a hydrogen atom, a $C_{1-4}$ alkylcarbonyl group, or a $C_{1-4}$ alkylcarbonyloxymethyl group.

(2) A compound of formula (II), a salt thereof, or a hydrate thereof:

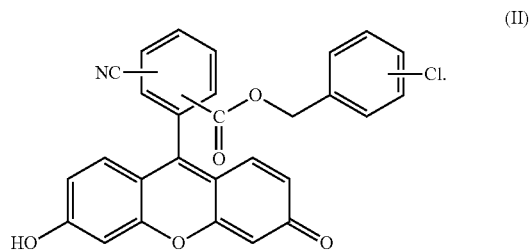

(3) A method for detecting enzymatic activity of a test substance, comprising:
(a) reacting the test substance with the compound of (1) or (2) above, a salt thereof or a hydrate thereof, and
(b) measuring a wavelength and intensity of fluorescence generated as a result of the reacting.
(4) The method of (3) above, wherein the enzymatic activity is an activity of one enzyme selected from the group consisting of nitrilase, nitrile hydratase, and amidase.
(5) The method of (3) above, wherein $R^1$ is —CN or —CH=CH—CN, and the enzymatic activity is the activity of nitrilase or nitrile hydratase.
(6) The method of (3) above, wherein $R^1$ is —CONH$_2$ or —CH=CH—CONH$_2$, and the enzymatic activity is the activity of amidase.
(7) The method of (3) above, wherein the measuring comprises flow cytometry.
(8) A fluorescent substrate comprising the compound of (1) or (2) above, a salt thereof, or a hydrate thereof, wherein the substrate is suitable for detecting an enzymatic activity of a nitrile-related enzyme.
(9) The substrate of (8) above, wherein the nitrile-related enzyme is a member selected from the group consisting of nitrilase, nitrile hydratase, and amidase.
(10) The substrate of (8) above, wherein $R^1$ is —CN or —CH=CH—CN, and the nitrile-related enzyme is nitrilase or nitrile hydratase.
(11) The substrate of (8) above, wherein $R^1$ is —CONH$_2$ or —CH=CH—CONH$_2$, and the nitrile-related enzyme is amidase.
(12) A kit, comprising the substrate of (8) above.
(13) The kit of (12) above, further comprising a cell lysis solution, a buffer and/or instructions for use.
(14) The method of (3) above, wherein a change in the wavelength and intensity of fluorescence is indicative of enzymatic activity.

By using the compound of the present invention, the enzymatic activity of a nitrile-related enzyme can be detected in a simple manner.

BEST MODES FOR CARRYING OUT THE INVENTION

Figure 1:
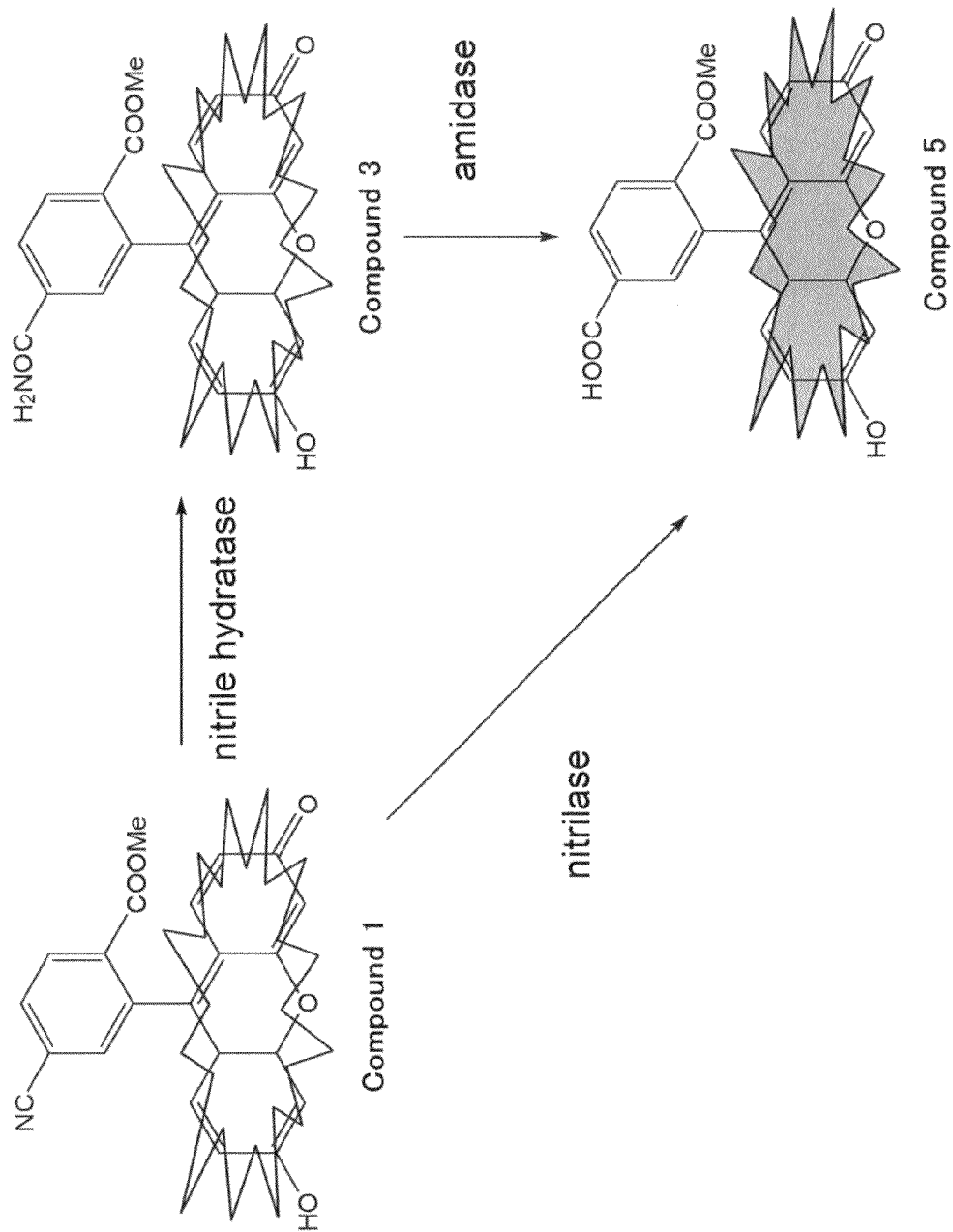
FIG. 1 shows the reaction path of a fluorescent substrate catalyzed by nitrile-related enzymes.

The present invention will be described in more detail below. The following embodiments are illustrated to describe the present invention, and it is not intended to limit the present invention only to these embodiments. The present invention can be implemented in various modes, without departing from the spirit of the present invention.

1. Summary

The present invention relates to a compound whose fluorescence will vary by the action of a nitrile-related enzyme (hereinafter also referred to as "the compound of the present invention") and a fluorescent substrate for detecting the enzymatic activity of a nitrile-related enzyme, which comprises the compound. The present invention also relates to a method for detecting the enzymatic activity of a test substance, which comprises reacting a test substance with the compound of the present invention and measuring the wavelength and intensity of fluorescence generated as a result of this reaction.

For use as a compound for detecting the enzymatic activity of a nitrile-related enzyme, the inventors of the present invention have attempted to synthesize a compound whose fluorescence will vary upon reaction with a nitrile-related enzyme. As a result of measuring fluorescence from the synthesized compound, the inventors of the present invention have found that fluorescence from a compound produced probably as a result of the enzymatic reaction is increased when compared to fluorescence from the compound before being subjected to the enzymatic reaction. Based on this finding, the inventors of the present invention have considered that the synthesized compound is useful as a fluorescent substrate for detecting the enzymatic activity of a nitrile-related enzyme, and thus have completed the present invention.

2. Compound

In the context of the present invention, a "compound whose fluorescence will vary by the action of a nitrile-related enzyme" is intended to mean a compound whose fluorescence will vary when a nitrile group (—CN) contained in the compound is converted into an amido group (—CONH$_2$) or a carboxyl group (—COOH) by the action of the enzyme or when an amido group contained in the compound is converted into a carboxyl group by the action of the enzyme. The compound of the present invention is not limited in any way, as long as it has a fluorophore and a nitrile group or an amido group, and as long as it is characterized in that fluorescence from its fluorophore will vary when the nitrile group in the compound is converted into an amido group or a carboxyl group or when the amido group in the compound is converted into a carboxyl group.

Moreover, although the mechanism of fluorescence variation by the action of a nitrile-related enzyme differs from compound to compound, the following explanation can be given for a compound represented by formula (I), by way of example.

This compound is substantially non-fluorescent or low fluorescent due to PeT (photo-induced electron transfer) before the reaction of a nitrile-related enzyme. However, once its nitrile group or amido group has been hydrolyzed as a result of the enzymatic reaction, PeT will no longer occur and fluorescence will be emitted. PeT is an electron transfer reaction caused by photo excitation.

For example, compound 1, which will be described later, is in a substantially non-fluorescent state because fluorescence from its excited fluorophore (i.e., its xanthene ring moiety) is quenched due to PeT from the xanthene moiety to the benzene ring moiety. However, when the nitrile group in compound 1 is hydrolyzed by nitrilase to give compound 5, PeT will no longer occur and compound 5 will emit fluorescence.

In the context of the present invention, a nitrile-related enzyme is intended to mean an enzyme that acts on nitrile-related compounds (compounds having a nitrile group and compounds having an amido group). Examples of such an enzyme include nitrilase, nitrile hydratase and amidase.

The "action" of such a nitrile-related enzyme is intended to mean hydration reaction or hydrolysis reaction.

A "variation" in fluorescence is intended to mean a shift in the fluorescence wavelength and/or a variation in the fluorescence intensity. Determination of whether fluorescence has "varied" or not can be accomplished based on the following criteria.

If the fluorescence intensity is increased, it is intended to mean a 1.5-fold or more increase, preferably a 2-fold or more increase, and more preferably a 3-fold or more increase, while if the fluorescence intensity is decreased, it is intended to mean a decrease to ⅔ or less, preferably a decrease to ½ or less, and more preferably a decrease to ⅓ or less. Likewise, if the fluorescence wavelength varies, it is intended to mean a 10 nm shift, preferably a 30 nm shift, and more preferably a 60 nm or more shift toward the longer or shorter wavelength side.

In the context of the present invention, examples of a compound whose fluorescence will vary by the action of a nitrile-related enzyme include a compound represented by the following formula (I).

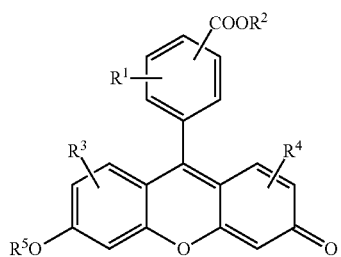
(I)

In formula (I), the substituent represented by $R^1$ is not limited in any way as long as it is a substituent capable of reacting with a nitrile-related enzyme, as exemplified by —CN, —CONH$_2$, —CH=CH—CN or —CH=CH—CONH$_2$.

The substituent represented by $R^2$ may be exemplified by a $C_{1-4}$ alkyl group or a halobenzyl group.

The substituents represented by $R^3$ and $R^4$ may be exemplified by a hydrogen atom, a halogen atom or a $C_{1-4}$ alkyl group.

The substituent represented by $R^5$ may be exemplified by a hydrogen atom, a $C_{1-4}$ alkylcarbonyl group or a $C_{1-4}$ alkylcarbonyloxymethyl group.

In the context of the present invention, a "$C_{1-4}$ alkyl group" is intended to mean a linear or branched alkyl group containing 1 to 4 carbon atoms, and examples include a methyl group, an ethyl group, a n-propyl group, an isopropyl group, a n-butyl group, an isobutyl group, a sec-butyl group, a tert-butyl group and so on, with a methyl group being preferred.

In the context of the present invention, a "halobenzyl group" is intended to mean a substituent derived from a benzyl group, in which at least one of the hydrogen atoms in the benzene ring contained in the benzyl group is replaced with a halogen atom, and examples include a 2-fluorobenzyl group, a 3-fluorobenzyl group, a 4-fluorobenzyl group, a 2-chlorobenzyl group, a 3-chlorobenzyl group, a 4-chlorobenzyl group, a 2-bromobenzyl group, a 3-bromobenzyl group, a 4-bromobenzyl group, a 2-iodobenzyl group, a 3-iodobenzyl group, and a 4-iodobenzyl group, with a 4-chlorobenzyl group being preferred.

In the context of the present invention, examples of a "$C_{1-4}$ alkylcarbonyl group" include an acetyl group, an ethylcarbonyl group, a propionylcarbonyl group, an isobutylcarbonyl group and so on, with an acetyl group being preferred.

In the context of the present invention, examples of a "$C_{1-4}$ alkylcarbonyloxymethyl group" include an acetoxymethyl group, an ethoxymethyl group, a propionyloxymethyl group, an isobutyryloxymethyl group and so on, with an acetoxymethyl group being preferred.

In the context of the present invention, examples of a "halogen atom" include a fluorine atom, a chlorine atom, a bromine atom and an iodine atom, with a fluorine atom or a chlorine atom being preferred.

The reason why $R^2$ is preferably a $C_{1-4}$ alkyl group, but not a hydrogen atom would be because if $R^2$ is a hydrogen atom, the electron density of the benzene ring is not sufficiently low to cause fluorophore quenching by photo-induced electron transfer. Namely, if $R^2$ is a hydrogen atom, the fluorescence intensity is high even before enzymatic reaction and hence it cannot be expected to obtain a large variation in the fluorescence intensity upon enzymatic reaction catalyzed by a nitrile-related enzyme. In contrast, if $R^2$ is a $C_{1-4}$ alkyl group, the electron density of the benzene ring is sufficiently low to cause fluorophore quenching by photo-induced electron transfer, so that it can be expected to obtain a variation in the fluorescence intensity upon enzymatic reaction.

Furthermore, the reason why $R^2$ is more preferably a halobenzyl group than an alkyl group is as follows.

According to Gaussian 09W-based orbital calculation (using 6-31+G*), LUMO (lowest unoccupied molecular orbital) at the benzene ring site is lower when $R^2$ is a halobenzyl group than when $R^2$ is an alkyl group. Namely, the efficiency of PeT (photo-induced electron transfer) from xanthene ring to benzene ring is higher when $R^2$ is a halobenzyl group than when $R^2$ is an alkyl group, so that background fluorescence can be reduced for the compound of the present invention to thereby cause a larger variation in the fluorescence intensity by the action of a nitrile-related enzyme. It should be noted that this finding was obtained after the inventors of the present invention had developed the compound represented by formula (I) and it cannot be predicted until the compound of the present invention has been developed.

Typical examples are shown below for the compound represented by formula (I) (wherein Me represents a methyl group). However, the compound represented by formula (I) is not limited to those listed below.

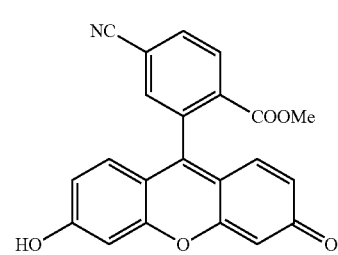

Compound 1

Compound 2
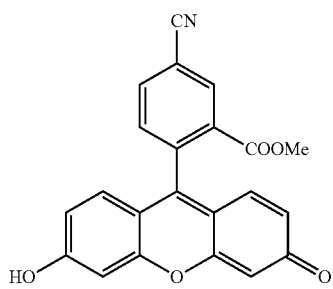
Compound 3
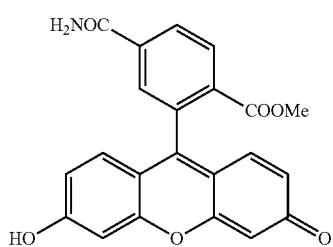
Compound 4
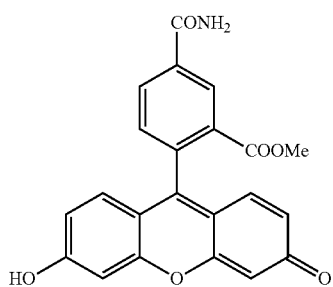
Compound 5
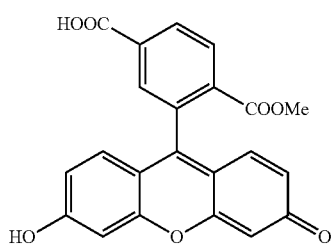
Compound 6
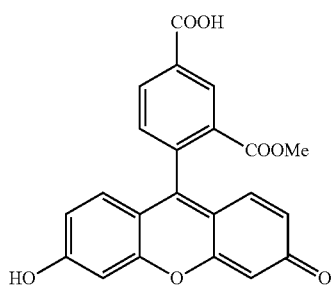
Compound 7
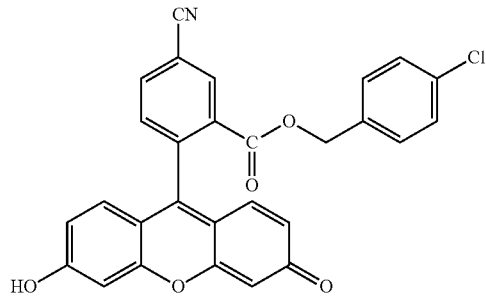
Compound 8
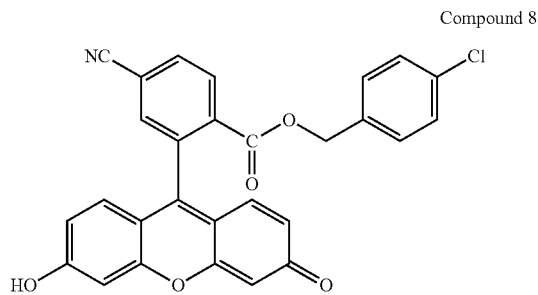
Compound 9
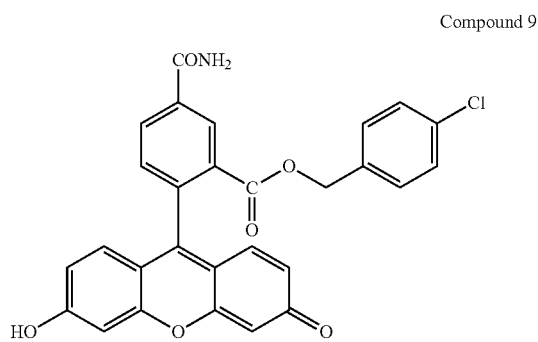
Compound 10
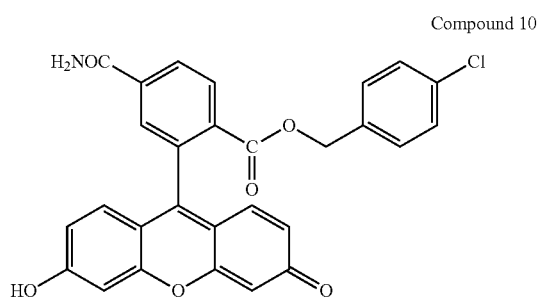 [SMILES: O=C(O)c1ccc(C(=O)OCc2ccc(Cl)cc2)c(-c2c3ccc(=O)cc-3oc3cc(O)ccc23)c1]
Compound 11
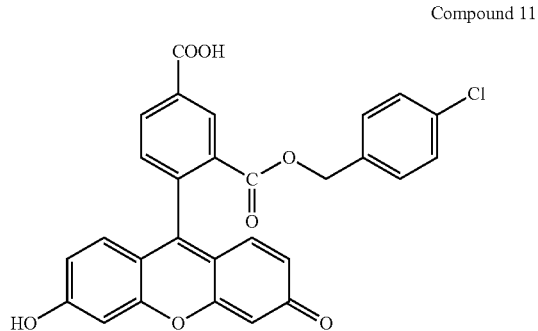

-continued

Compound 12

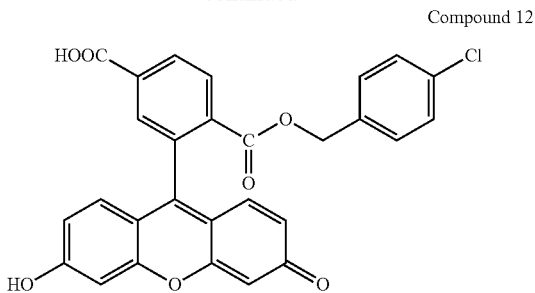

In the present invention, compound 7 shown above is also referred to as 5-cyanofluorescein-4-chlorobenzyl ester (CFCB).

In another embodiment of the present invention, examples of a compound whose fluorescence will vary by the action of a nitrile-related enzyme include a compound represented by formula (II), which falls within the compound represented by formula (I).

(II)

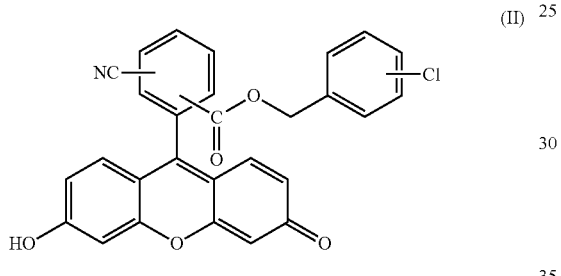

Examples of such a compound represented by formula (II) include 5-cyanofluorescein-4-chlorobenzyl ester, 4-cyanofluorescein-4-chlorobenzyl ester, 3-cyanofluorescein-4-chlorobenzyl ester, 5-cyanofluorescein-3-chlorobenzyl ester, 5-cyanofluorescein-2-chlorobenzyl ester, 4-cyanofluorescein-3-chlorobenzyl ester, 4-cyanofluorescein-2-chlorobenzyl ester, 3-cyanofluorescein-3-chlorobenzyl ester, 3-cyanofluorescein-2-chlorobenzyl ester and so on, with 5-cyanofluorescein-4-chlorobenzyl ester being preferred.

The above compound represented by formula (I) may form a salt or hydrate thereof. Any salt is possible as long as it has the effect of the present invention, and such a salt may be formed with either an acid or a base.

Examples of a salt with an acid include salts with inorganic acids (e.g., hydrochloride salt, hydrobromide salt, sulfate salt, phosphate salt), as well as salts with organic acids such as formic acid, acetic acid, lactic acid, succinic acid, fumaric acid, maleic acid, citric acid, tartaric acid, benzoic acid, methanesulfonic acid, benzenesulfonic acid, p-toluenesulfonic acid, trifluoroacetic acid and so on.

Examples of a salt with a base include alkali metal salts (e.g., sodium salt, potassium salt), alkaline earth metal salts (e.g., calcium salt, magnesium salt), salts with organic bases such as trimethylamine, triethylamine, pyridine, picoline, dicyclohexylamine, N,N'-dibenzylethylenediamine and so on (organic amine salts), as well as ammonium salts.

Alternatively, the compound of the present invention may not form any salt, i.e., may be in a so-called free form.

The compound represented by formula (I) may be prepared in the following manner.

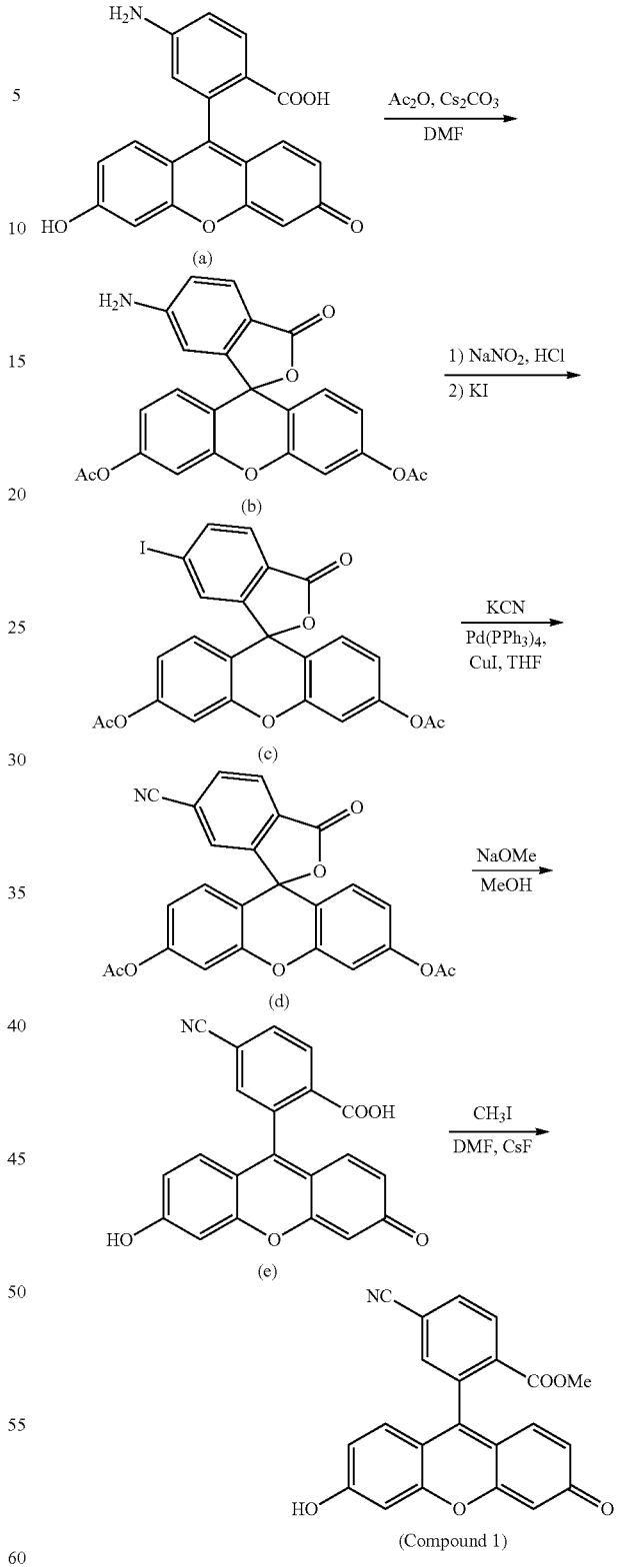

First, compound (a) to be used as a starting material can be obtained by being purchased from Tokyo Chemical Industry (TCI) Co., Ltd., Japan. Compound (a) is then reacted in DMF with $Ac_2O$ and $Cs_2CO_3$ at room temperature for 1 hour to obtain compound (b). Compound (b) is then dissolved in 12 N HCl, and $NaNO_2$ is added dropwise thereto on an ice bath, followed by stirring. After stirring for 30 minutes at 0° C., KI dissolved in water is added dropwise and the mixture is stirred for 10 minutes. The mixture is returned to room temperature and reacted for 1 hour to obtain compound (c). Compound (c) is further reacted in THF with KCN under reflux at about 80° C. for 3 hours in the presence of CuI and Pd(PPh$_3$)$_4$ as a catalyst to obtain compound (d). Compound (d) is reacted in MeOH with MeONa at room temperature for 10 minutes to obtain compound (e). Finally, compound (e) is reacted in CsF and DMF with 1 equivalent of CH$_3$I at room temperature for about 1 hour to obtain compound 1.

Additionally, the compound represented by formula (I), for example, compound 7 shown above can be prepared in the following manner.

First, compound 2 represented by the following formula can be used as a starting material.

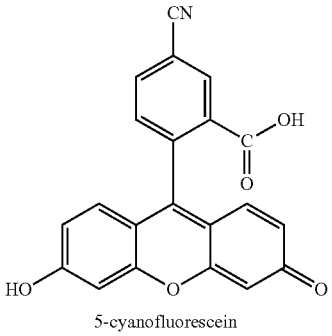 [SMILES: N#Cc1ccc(-c2c3ccc(=O)cc-3oc3cc(O)ccc23)c(C(=O)O)c1]
5-cyanofluorescein

To DMF containing 5-cyanofluorescein dissolved therein, 4-chlorobenzyl alcohol, 1-ethyl-3-(3-dimethylaminopropyl) carbodiimide hydrochloride and N,N-dimethyl-4-aminopyridine are added and stirred at room temperature for several hours. The reaction mixture is concentrated with an evaporator and then partitioned by addition of dichloromethane and saturated aqueous ammonium chloride to extract the organic phase. This organic phase is partitioned again by addition of saturated aqueous sodium chloride to extract the organic phase, which is then concentrated with an evaporator. The resulting residue is purified by fully automatic column chromatography (dichloromethane/methanol=96/4) to thereby obtain compound 7. Conditions (e.g., the amount of each reagent, reaction time, temperature) used for this synthesis procedure may be determined as appropriate by those skilled in the art.

3. Fluorescent Substrate

The above compound represented by formula (I), a salt thereof or a hydrate thereof may be used as a fluorescent substrate for detecting the enzymatic activity of a nitrile-related enzyme.

An explanation will be given below of the mechanism by which the above compound represented by formula (I) generates fluorescence.

The above compound represented by formula (I) is substantially non-fluorescent due to PeT (photo-induced electron transfer) before the reaction of a nitrile-related enzyme. However, once its nitrile group or amido group has been hydrolyzed as a result of the enzymatic reaction, PeT will no longer occur and fluorescence will be emitted. PeT is an electron transfer reaction caused by photoexcitation.

For example, compound 1 is in a substantially non-fluorescent state because fluorescence from its excited fluorophore (i.e., its xanthene ring moiety) is quenched due to PeT from the xanthene moiety to the benzene ring moiety. However, when the nitrile group in compound 1 is hydrolyzed by nitrilase to give compound 5, PeT will no longer occur and compound 5 will emit fluorescence (FIG. 1).

If fluorescence can be detected, such a result indicates that a nitrile-related enzyme is present in a test sample or a test substance contained in the sample has enzymatic activity as a nitrile-related enzyme.

In the context of the present invention, examples of a nitrile-related enzyme include, but are not limited to, nitrilase, nitrile hydratase, and amidase.

A preferred nitrile-related enzyme is nitrilase or nitrile hydratase for compounds represented by formula (I) in which R$^1$ is —CN or —CH=CH—CN, while a preferred nitrile-related enzyme is amidase for compounds represented by formula (I) in which R$^1$ is —CONH$_2$ or —CH=CH—CONH$_2$.

4. Detection Method for Enzymatic Activity

The present invention provides a detection method for enzymatic activity. More specifically, the present invention provides a method for detecting the enzymatic activity of a test substance, which comprises the steps of: (a) reacting a test substance with a compound whose fluorescence will vary by the action of a nitrile-related enzyme or a fluorescent substrate comprising the compound; and (b) measuring the wavelength and intensity of fluorescence generated as a result of the reaction in step (a).

In the context of the present invention, the test substance is not limited in any way, as long as it is a protein having the enzymatic activity of a nitrile-related enzyme or is predicted to contain DNA encoding such a protein. Examples include substances contained in metagenomic libraries obtained from the natural environment or mutated enzyme gene libraries, etc. Further, such test substances encompass not only DNAs and proteins, but also cells producing these proteins. Examples of such cells include bacteria, fungi (e.g., yeast, filamentous fungi), plant cells, animal cells and so on. These cells further encompass cells which have been transformed to express a protein having the enzymatic activity of a nitrile-related enzyme. Examples of these transformed cells include, but are not limited to, microbial cells for which host vector systems have been developed, as exemplified by bacteria of the genera *Escherichia*, *Bacillus*, *Pseudomonas*, *Serratia*, *Brevibacterium*, *Corynebacterium*, *Streptococcus*, *Lactobacillus*, *Rhodococcus* and *Streptomyces*, yeast of the genera *Saccharomyces*, *Kluyveromyces*, *Schizosaccharomyces*, *Zygosaccharomyces*, *Yarrowia*, *Trichosporon*, *Rhodosporidium*, *Pichia* and *Candida*, filamentous fungi of the genera *Neurospora*, *Aspergillus*, *Cephalosporium* and *Trichoderma*, etc.

A metagenomic library refers to a genomic library constructed from the DNAs of various microorganisms present in the natural environment, which is prepared by directly extracting DNAs from environmental samples and organizing the resulting DNAs into a library without culturing the microorganisms. A mutated enzyme gene library refers to a library prepared by introducing random mutations into DNAs encoding known enzymes and organizing the resulting DNAs into a library.

Procedures for metagenomic library preparation can be found in, e.g., JP 2007-159417 A, while procedures for mutated enzyme gene library preparation can be found in, e.g., Molecular Cloning: A laboratory Manual, 2nd Ed., Cold Spring Harbor Laboratory, Cold Spring Harbor, N.Y., 1989 and Current Protocols in Molecular Biology, Supplement 1 to 38, John Wiley & Sons (1987-1997). Those skilled in the art would be able to prepare the above libraries based on these documents.

More specifically, the detection method of the present invention may be accomplished in the following manner, by way of example.

In a case where a metagenomic library or a mutated enzyme gene library is used as a test substance, DNAs contained in these libraries are each transfected into cells to prepare a library of transformants. Then, the transformants are introduced with the compound or fluorescent substrate of the present invention to thereby cause reaction between the protein produced in each transformant and the compound or fluorescent substrate of the present invention, followed by measuring the wavelength and intensity of fluorescence generated as a result of the above reaction. For measurement of fluorescence, it is possible to use a fluorescence detection instrument such as a fluorescence spectrophotometer or an imager, or flow cytometry, etc.

Flow cytometry refers to a laser-based technique for measuring, e.g., the size, DNA content, cell surface antigen distribution and/or intracellular enzymatic activity of a single cell passing through a flow cell by means of light scattering or fluorimetry. In the method of the present invention, a test substance and a compound whose fluorescence will vary by the action of a nitrile-related enzyme are reacted with each other, and fluorescence generated as a result of this reaction can be measured using flow cytometry.

Flow cytometry may be accomplished by using a commercially available flow cytometer in accordance with the manufacturer's instructions. A flow cytometer is a device comprising a laser generator, an optical system, a nozzle and a data processing system, and it allows automatic separation and fluorescence analysis of fluorescence-emitting cells, as well as their computer-aided analysis. In particular, a flow cytometer with cell sorting functions (i.e., a cell sortor) allows high-speed screening and sorting to collect only cells emitting desired fluorescence. In such a cell sortor, a nozzle in the cell sortor is ultrasonically vibrated to form droplets in a sheath flow, and droplets are charged at the moment when formed from a sheath flow containing target cells. The charged droplets are attracted to a negatively charged deflection plate and collected into a tube. In this way, cells having desired fluorescence are screened and sorted. Examples of a commercially available flow cytometer include a BD FACS-Calibur™ flow cytometer, a BD FACSAria™ III cell sortor (Nippon Becton Dickinson), etc.

In the present invention, fluorescence generated as a result of reaction between a test substance and the compound of the present invention is measured using flow cytometry, whereby cells emitting desired fluorescence, i.e., cells containing a substance having the desired enzymatic activity can be screened at high speed for separation or sorting. In the case of not using flow cytometry, fluorescence measurement can be performed on several hundreds of cells per day. On the other hand, in the case of using flow cytometry in a FACS (fluorescence-activated cell sorting) system, fluorescence measurement can be performed on several tens of thousands to several million cells per day. This means that if the number of cells processable in FACS is several hundred per second, the measurement of one million cells will be completed within 1 or 2 hours, which in turn means that in the case of using higher performance FACS (about 7000 cells per second), the measurement of one million cells will be completed within several minutes.

Thus, the use of flow cytometry for fluorescence measurement in the method of the present invention allows not only automatic and faster detection of the enzymatic activity of a test substance, but also automatic and faster screening and sorting (high-throughput screening) of cells containing a substance having the desired enzymatic activity.

5. Kit

The present invention provides a kit for detecting the enzymatic activity of a nitrile-related enzyme, which contains a fluorescent substrate comprising the above compound represented by formula (I). The kit of the present invention may further comprise any other constituent elements (e.g., a cell lysis solution, a buffer, instructions for use) required for detecting the enzymatic activity of a nitrile-related enzyme, as appropriate, in addition to the fluorescent substrate of the present invention.

EXAMPLES

The present invention will be further described in more detail by way of the following illustrative examples, which are not intended to limit the scope of the invention.

Example 1

1. Synthesis of Compounds Whose Fluorescence Will Vary by the Action of a Nitrile-Related Enzyme (1) Compounds Represented by Formula (I)

As compounds whose fluorescence will vary by the action of a nitrile-related enzyme, typical examples are shown below for the compound represented by formula (I) in the present invention (wherein Me represents a methyl group).

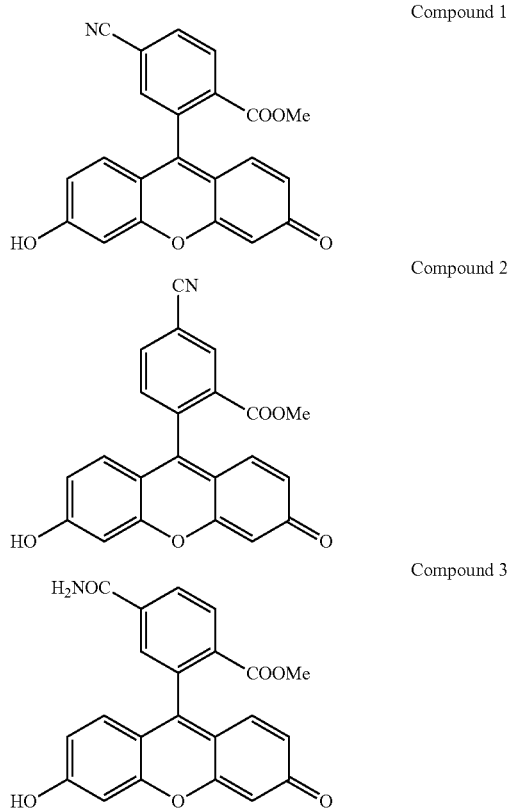

Compound 4
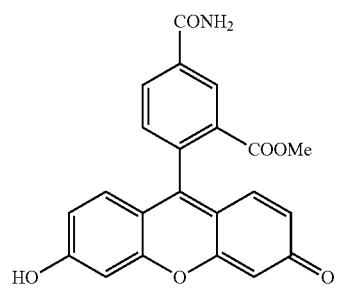
Compound 5
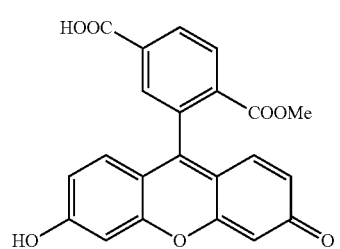
Compound 6
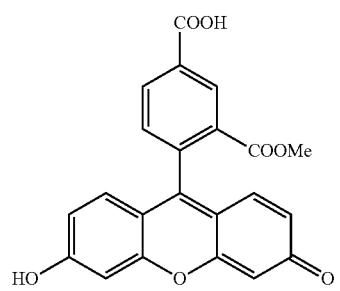
Compound 7
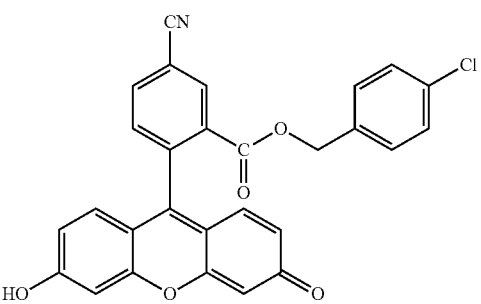
Compound 8
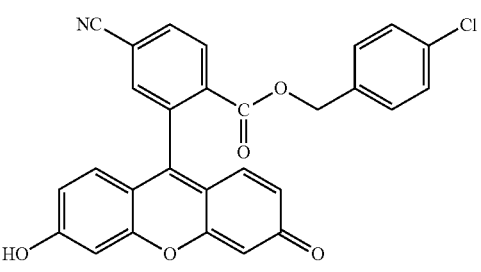
Compound 9
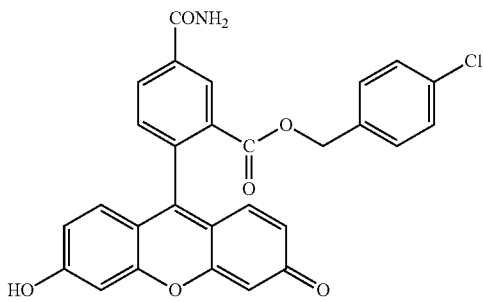
Compound 10
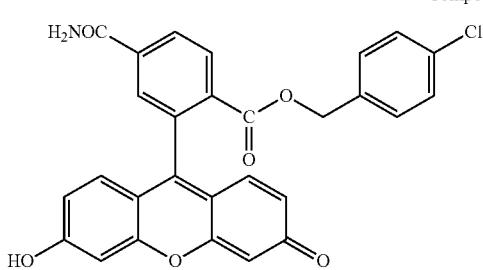
Compound 11
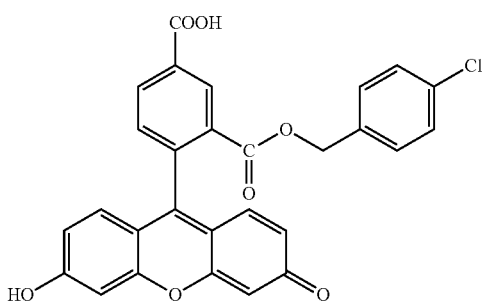
Compound 12
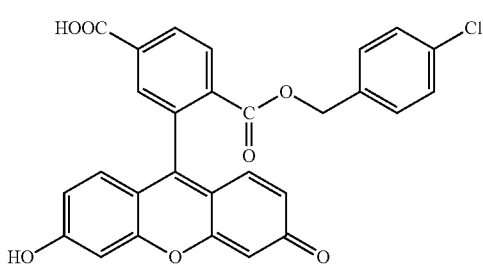
(2) Synthesis of Compounds Represented by Formula (I)
Compound 1 was synthesized according to scheme 1 shown below.
<Scheme 1: Synthesis of compound 1>
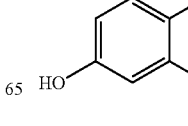
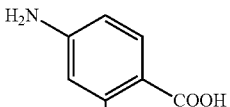
(a)

-continued

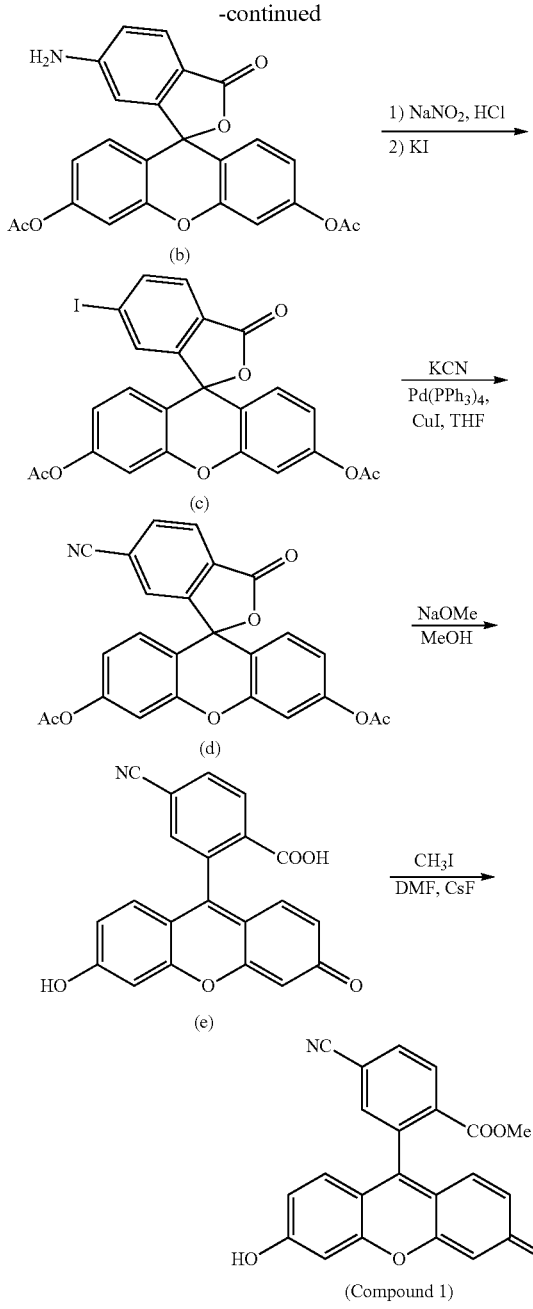

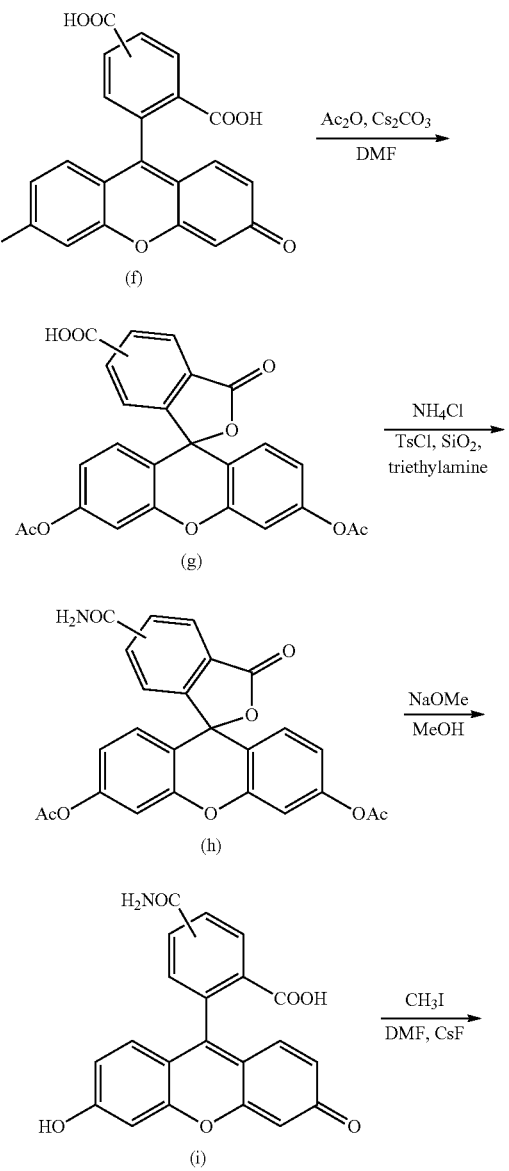

Compound (a) to be used as a starting material was obtained by being purchased from Tokyo Chemical Industry (TCI) Co., Ltd., Japan. Compound (a) was then reacted in DMF with Ac$_2$O and Cs$_2$CO$_3$ at room temperature for 1 hour to give compound (b). Compound (b) was then dissolved in 12 N HCl, and NaNO$_2$ is added dropwise thereto on an ice bath, followed by stirring. After stifling for 30 minutes at 0° C., KI dissolved in water was added dropwise and the mixture was stirred for 10 minutes. The mixture was returned to room temperature and reacted for 1 hour to give compound (c). Compound (c) was further reacted in THF with KCN under reflux at about 80° C. for 3 hours in the presence of CuI and Pd(PPh$_3$)$_4$ as a catalyst to give compound (d). Compound (d) was reacted in MeOH with MeONa at room temperature for 10 minutes to give compound (e). Finally, compound (e) was reacted in CsF and DMF with 1 equivalent of CH$_3$I at room temperature for about 1 hour to give compound 1.

Compound 1

$^1$H NMR (300 MHz, CD$_3$OD): δ 6.82 (d, 2H, J=9.33 Hz), 6.68-6.73 (m, 4H), 3.65 (s, 3H), 7.89 (d, 1H, J=1.11 Hz), 8.14 (dd, 1H, J=1.47, 8.25 Hz), 8.40 (d, 1H, J=8.10 Hz) HRMS (ESI-): Calcd for [M-H]$^-$, 370.0716. Found, 370.0672 (-4.38 mmu)

Compound 2 was also synthesized in a manner similar to scheme 1 above.

Compound 2

$^1$H NMR (300 MHz, (CD$_3$OD): δ 3.66 (s, 3H), 6.67-6.74 (m, 4H), 6.96-6.99 (m, 2H), 6.64 (d, 1H, J=8.07 Hz), 8.18 (dd, 1H J=8.07, 1.47 Hz), 8.61 (d, 1H, J=1.47 Hz) HRMS (ESI-): Calcd for [M-H]$^-$, 370.07155. Found, 370.06831 (-3.24 mmu)

Compounds 3 and 4 were synthesized according to scheme 2 shown below.

Scheme 2: Synthesis of 4(5)-CONH$_2$ fluorescein methyl esters

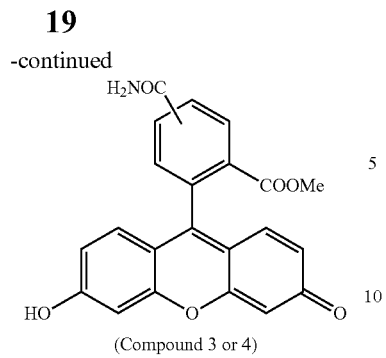

(Compound 3 or 4)

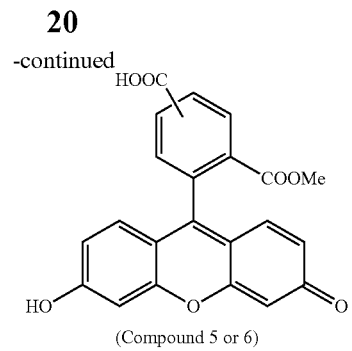

(Compound 5 or 6)

First, compound (f) to be used as a starting material was obtained by being purchased from SIGMA. Compound (f) was then reacted in DMF with Ac$_2$O and Cs$_2$CO$_3$ at room temperature for 1 hour to give compound (g) (yield: 96%). Compound (g) was then reacted in TsCl and triethylamine with NH$_4$Cl supported on silica gel at room temperature for 10 minutes to give compound (h). Compound (h) was further reacted in MeOH with MeONa at room temperature for 10 minutes to give compound (i). Finally, compound (i) was reacted in CsF and DMF with 1 equivalent of CH$_3$I at room temperature for 1 hour to give compounds 3 and 4 (yield: 2.3%).

Compound 3

$^1$H NMR (300 MHz, CD$_3$OD): δ 8.37 (d, 1H, J=8.07 Hz), 8.23 (dd, 1H, J=8.07, 1.47 Hz), 7.89 (d, 1H, J=1.47 Hz), 7.01 (m, 2H), 6.64 (m, 4H), 3.64 (s, 3H) HRMS (ESI+): Calcd for [M+H]$^+$, 390.09776. Found, 390.09473 (−3.04 mmu)

Compound 4

$^1$H NMR (300 MHz, CD$_3$OD): δ 8.79 (d, 1H, J=2.20 Hz), 8.30 (dd, 1H, J=8.07, 2.20 Hz), 7.55 (d, 1H, J=8.07 Hz), 7.00 (m, 2H), 6.72 (m, 4H), 3.66 (s, 1H) HRMS (ESI+): Calcd for [M+H]$^+$, 390.09776. Found, 390.09457 (−3.19 mmu)

Compounds 5 and 6 were synthesized according to scheme 3 shown below.

Scheme 3: Synthesis of 4(5)-COOH fluorescein methyl esters

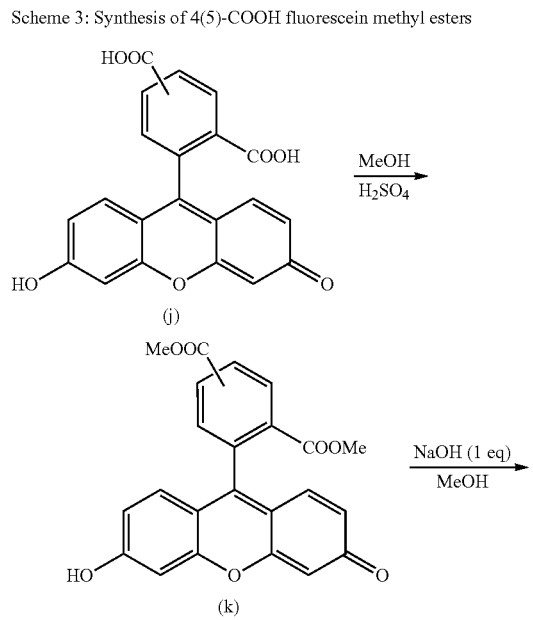

Compound (j) was reacted in H$_2$SO$_4$ with MeOH under reflux at 100° C. for 1 hour to give compound (k) (yield: 8.6%). Compound (k) was then reacted in MeOH with 1 equivalent of NaOH under reflux at 100° C. for 2 hours to give compounds 5 and 6 (trace).

Compounds 5 and 6

HRMS (ESI+): Calcd for [M+H]$^+$, 391.08178. Found, 391.08536 (+3.57 mmu)

Compound 7 was synthesized in the following manner.

First, compound 2 as a starting material was obtained by reference to the method described above.

Next, to DMF (2 mL) containing 5-cyanofluorescein (49.9 mg, 0.140 mmol) dissolved therein, 4-chlorobenzyl alcohol (203.7 mg, 1.43 mmol), 1-ethyl-3-(3-dimethylaminopropyl)carbodiimide hydrochloride (30.5 mg, 0.159 mmol) and N,N-dimethyl-4-aminopyridine (6.4 mg, 0.0524 mmol) were added and stirred at room temperature for 6 hours. The reaction mixture was concentrated with an evaporator and then partitioned by addition of dichloromethane and saturated aqueous ammonium chloride to extract the organic phase. This organic phase was partitioned again by addition of saturated aqueous sodium chloride to extract the organic phase, which was then concentrated with an evaporator. The resulting residue was purified by fully automatic column chromatography (dichloromethane/methanol=96/4) to give compound 7 (6.1 mg, 0.0127 mmol) as an orange solid (yield: 9.1%).

Compound 7

$^1$H NMR (400 MHz, CD$_3$OD) δ: 8.61 (d, 1H, J=1.3 Hz), 8.16 (dd, 1H, J=1.7 and 8.0 Hz), 7.58 (dd, 1H, J=0.3 and 8.0 Hz), 7.17 (d, 2H, J=8.5 Hz), 6.92 (d, 2H, J=9.2 Hz), 6.83 (d, 2H, J=8.5 Hz), 6.65 (dd, 2H, J=2.1 and 9.2 Hz), 6.59 (d, 2H, J=2.1 Hz), 4.93 (s, 2H). HRMS (ESI−): m/z calculated for [M−H]$^-$ 480.06442. found 480.06597.

2. Measurement of Fluorescence and Fluorescence Quantum Yield for Compounds

Compounds 1 to 6 obtained above were measured for their fluorescence. The results obtained are shown in FIG. 2.

Figure 2:
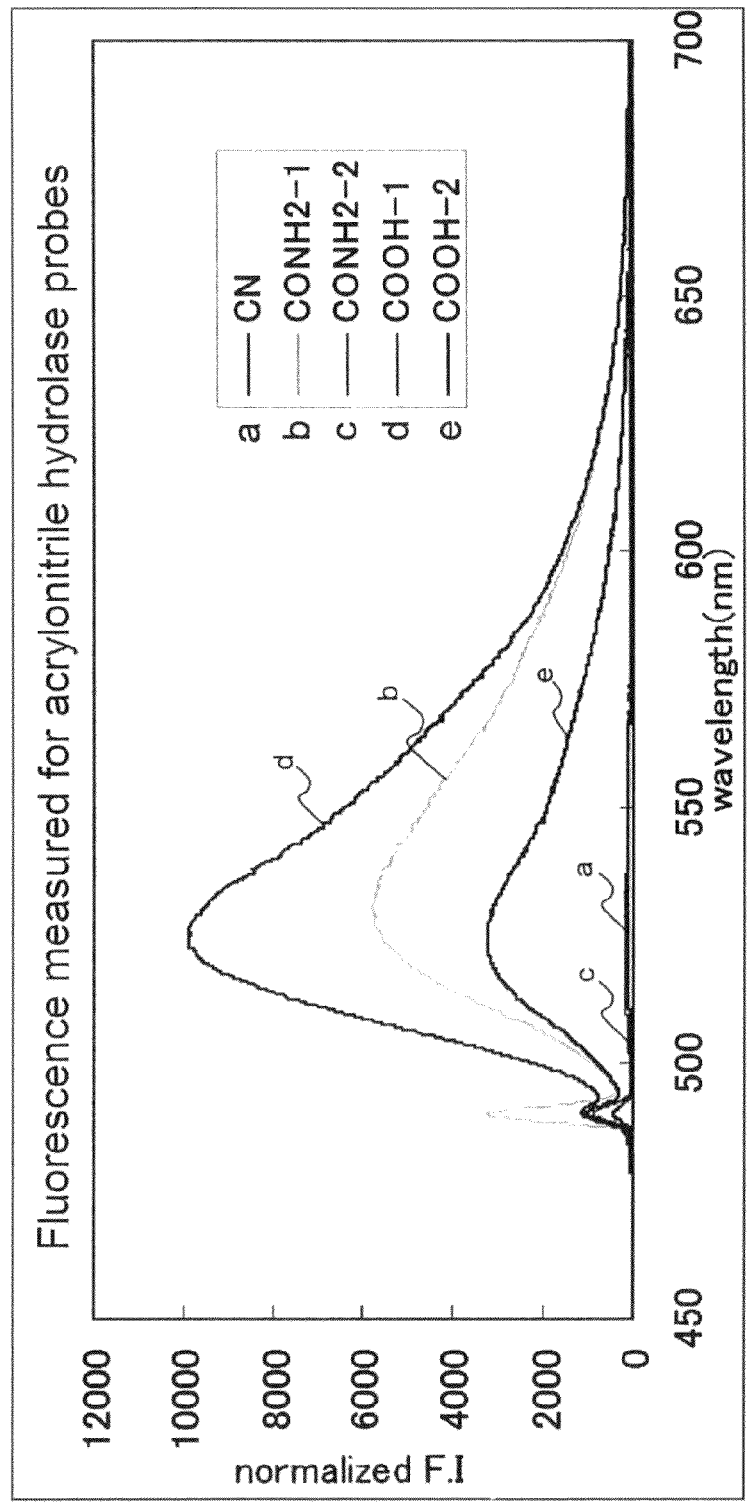
FIG. 2 shows the results of fluorescence measurement performed on fluorescent substrates.

In FIG. 2, "CN" represents compound 1, "CONH$_2$-1" represents compound 4, and "CONH$_2$-2" represents compound 3. Likewise, "COOH-1" represents 5-COOH fluorescein, while "COOH-2" represents a mixture of compounds 5 and 6.

Compounds 1 to 6 were also measured for their fluorescence quantum yield ($\Phi_{fl}$). As a result, compounds 1 to 6 were found to have a fluorescence quantum yield of 0.007, 0.161, 0.018, 0.397, 0.0729 and 0.565, respectively. With respect to compounds 5 and 6, it should be noted that their fluorescence quantum yields were calculated as values in isolated form based on the concentration ratio determined by HPLC.

These measurement results are shown below.

Compound 1

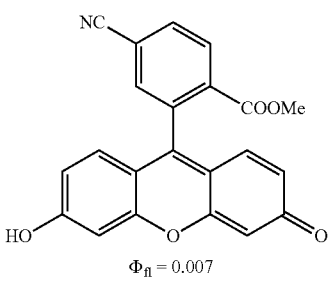

$\Phi_{fl}$ = 0.007

Compound 2

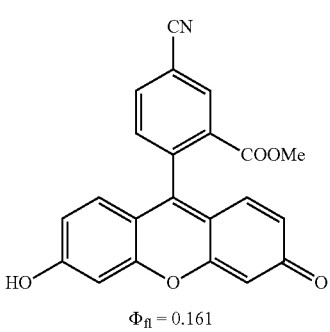

$\Phi_{fl}$ = 0.161

Compound 3

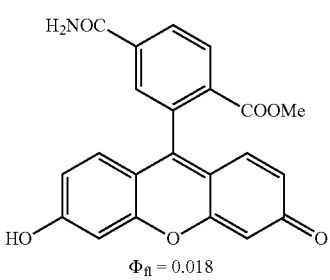

$\Phi_{fl}$ = 0.018

Compound 4

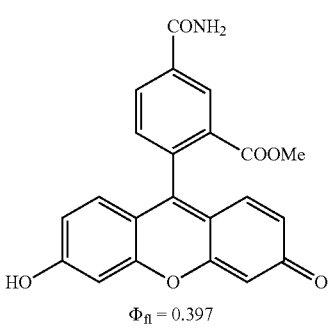

$\Phi_{fl}$ = 0.397

Compound 5

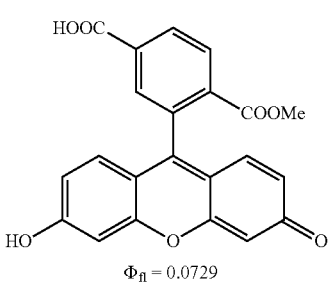

$\Phi_{fl}$ = 0.0729

Compound 6

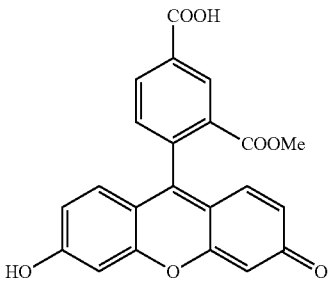

$\Phi_{fl}$ = 0.565

TABLE 1

| Substituent | —CN (compound 1) | —CONH$_2$ (compound 3) | —COOH (compound 5) |
| --- | --- | --- | --- |
| Fluorescence quantum yield ($\Phi_{fl}$) | 0.007 | 0.018 | 0.0729 |

TABLE 2

| Substituent | —CN (compound 2) | —CONH$_2$ (compound 4) | —COOH (compound 6) |
| --- | --- | --- | --- |
| Fluorescence quantum yield ($\Phi_{fl}$) | 0.161 | 0.397 | 0.565 |

The above results indicated that compound 1 was substantially non-fluorescent and showed little increase in fluorescence even when converted into compound 3 by hydrolysis of the nitrile group (—CN) into an amido group (—CONH$_2$), but it showed a large increase in fluorescence when converted into compound 5 by further hydrolysis of the amido (Table 1). This result showed that compound 1 was able to be used as a fluorescent substrate for detecting the enzymatic activity of nitrilase.

Likewise, it was also shown that compound 3 was able to be used as a fluorescent substrate for detecting the enzymatic activity of amidase, because compound 3 was substantially non-fluorescent and was converted into fluorescent compound 5 upon hydrolysis of the amido group in compound 3.

Further, compound 2 was found to be a candidate for a fluorescent substrate for detecting the activity of nitrile hydratase and nitrilase, because its fluorescence intensity increased as the nitrile group (—CN) was converted into an amido group (—CONH$_2$) and further into a carboxyl group (—COOH) (Table 2).

In view of the foregoing, the compounds designed and synthesized in this example were found to serve as fluorescent substrates for enzymatic activity detection because of having fluorescence properties through which the enzymatic reactions of nitrilase, nitrile hydratase and amidase can be visualized as changes in fluorescence.

Moreover, absorption spectra and fluorescence quantum yields (Cl$_O$) of compound 7 were measured and compared with that of compound 2.

The absorption spectra and fluorescence quantum yields of the compounds were measured as follows.

A 1 mM solution of compound 7 in DMSO was prepared and this solution was added to 200 mM sodium phosphate buffers of pH 2 to 12 to prepare 1 μM sample solutions containing 0.1% DMSO. These sample solutions were measured for their absorption spectra between 300 nm and 600 nm with an ultraviolet and visible spectrophotometer UV-2450 (Shimadzu Corporation, Japan). In addition, a 0.2 µM sample solution of compound 7 containing 0.02% DMSO in 200 mM sodium phosphate buffer (pH 7.3) was prepared and measured for its fluorescence quantum yield using an absolute PL quantum yield measurement system, Quantaurus-QY (Hamamatsu Photonics K.K., Japan), under irradiation with 470 nm excitation light.

Figure 6:
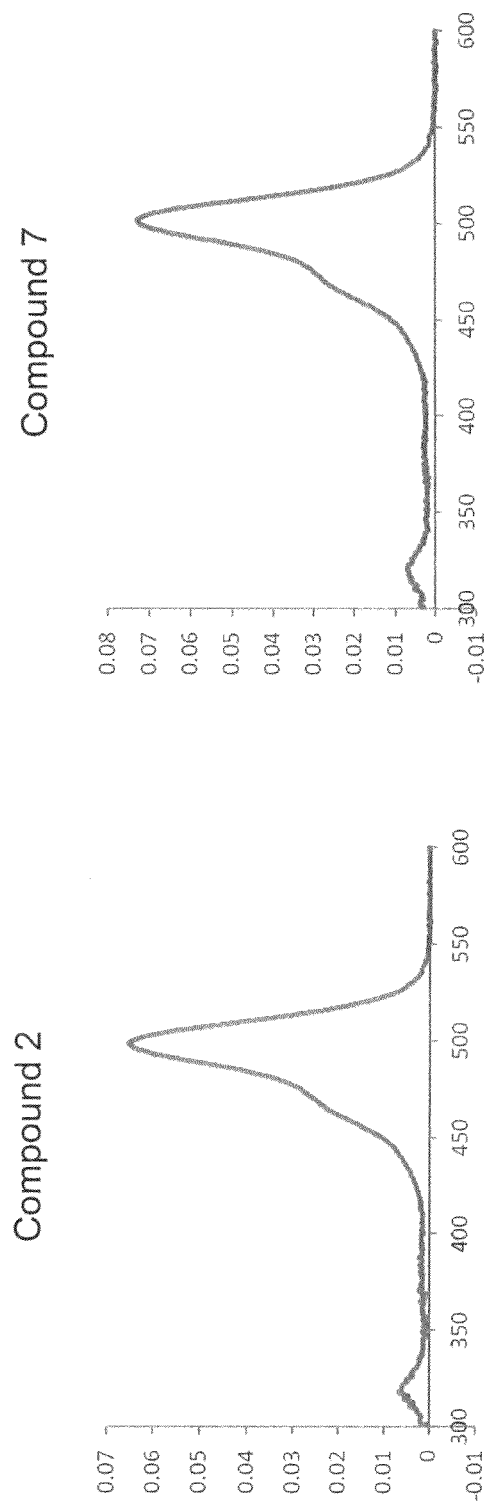
FIG. 6 shows absorption spectra obtained for compound 7 and compound 2.

As a result, compound 7 and compound 2 showed similar absorption spectra (FIG. 6).

On the other hand, compound 7 and compound 2 were found to have fluorescence quantum yields of 0.154 and 0.172, respectively, indicating that the fluorescence quantum yield of compound 7 was lower than that of compound 2.

This result would be due to the fact that LUMO (lowest unoccupied molecular orbital) at the benzene site of compound 7 is lower than LUMO of compound 2.

Example 2

Nitrile Hydratase-Catalyzed Reaction

1. Preparation of Crude Nitrile Hydratase Solution (Cell-Free Extract)

Plasmid pSJ034 designed to constitutively express *Rhodococcus rhodochrous* strain J1-derived nitrile hydratase in *Rhodococcus* bacterial cells was introduced into *Rhodococcus rhodochrous* strain ATCC12674. pSJ034 has been prepared from plasmid pSJ023 as described in the specification of JP 10-337185 A. pSJ023 was deposited as a transformant, *R. rhodochrous* ATCC12674/pSJ023 (FERM BP-6232), with the International Patent Organism Depositary, the National Institute of Advanced Industrial Science and Technology.

*Rhodococcus rhodochrous* strain ATCC12674 was transformed with plasmid pSJ034 to prepare ATCC12674/pSJ034. The strain 12674 was also transformed with vector pK4 for use in a control experiment.

Transformation of the strain ATCC 12674 was accomplished as follows. Cells of the strain ATCC12674 at the logarithmic growth phase were collected with a centrifugal separator, washed three times with ice-cold sterilized water, and suspended in sterilized water. The plasmid solution prepared above (1 µl) and the cell suspension (10 µl) were mixed together and cooled on ice. This mixture was transferred to a cuvette for a gene transfer device, Gene Pulser (BIO RAD), and electrically pulsed in this device at 2.0 KV at 200 OHMS. The electrically pulsed solution was allowed to stand under ice cooling for 10 minutes and then incubated at 37° C. for 10 minutes, followed by addition of 500 µl of MYK medium (0.5% polypeptone, 0.3% Bactoyeast extract, 0.3% Bactomalt extract, 0.2% $K_2HPO_4$, 0.2% $KH_2PO_4$). The resulting solution was allowed to stand at 30° C. for 5 hours and then applied onto a 50 µg/ml kanamycin-containing MYK agar medium, followed by culturing at 30° C. for 3 days. The resulting colony was cultured and confirmed to carry the plasmid.

The colony was cultured as follows. The colony was inoculated into a kanamycin (50 mg/L)-containing MYK medium (10 ml) and pre-cultured at 30° C. for 24 hours. The culture broth was taken in a volume of 1 ml and added to 100 ml of the same medium, followed by shaking culture at 30° C. for 48 hours. The resulting culture broth was centrifuged (3,700×g, 10 minutes, 4° C.) to collect the cells, which were then washed with 10 mM sodium phosphate buffer (pH 7.0) and suspended in the same buffer.

1 ml of the resulting cell suspension was homogenized for 3 minutes under ice cooling with an ultrasonic homogenizer VP-15S (TAITEC Co., Ltd, Japan) under the following conditions: output control 4, DUTY CYCLE 40%, PULS, TIMER=B mode 10 s. The homogenate was then centrifuged (10,000×g, 5 minutes, 4° C.) and the resulting supernatant was collected as a cell-free extract.

2. Enzymatic Reaction

10 µL of sodium phosphate buffer (pH 7.0), 75 µL of sterilized water and 5 µL of 0.01 mM nitrile fluorescent substrate (compound 2: dissolved in 10% DMSO) were mixed together and pre-incubated at 30° C. The cell-free extract prepared above (10 µL) was added to initiate the reaction. After the reaction at 30° C. for 1 hour, the mixture was transferred to a 96-well microplate and fluorescence was detected with a fluorescence imager (BioRad Pharos FX molecular Imager, excited at 488 nm, detected at 530 nm).

Figure 3:
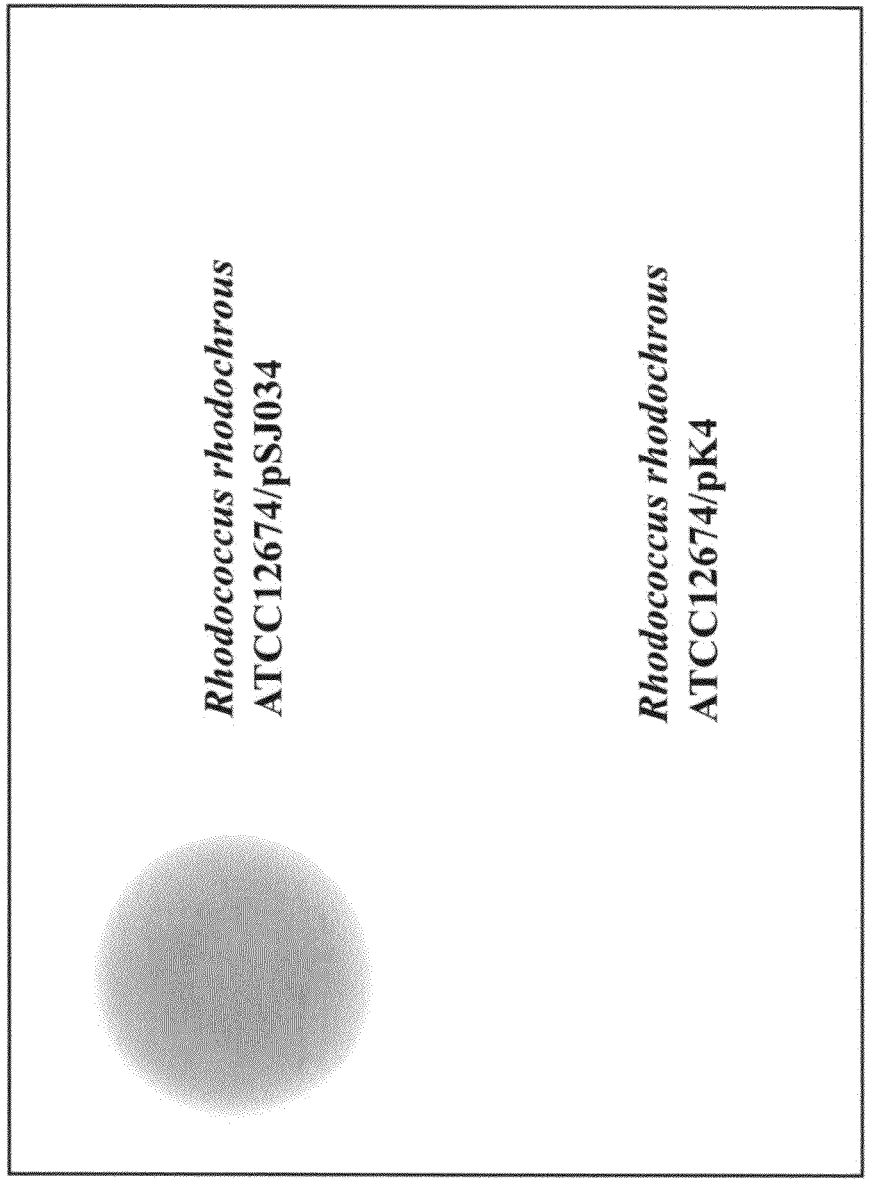
FIG. 3 shows the detection results of a nitrile hydratase activity-induced increase in the fluorescence intensity of a fluorescent substrate.

The results obtained are shown in FIG. 3. The cell-free extract obtained from the vector pK4-carrying recombinant used as a control sample showed no change in fluorescence, whereas there was a significant increase in the intensity of fluorescence when using the nitrile hydratase-expressing recombinant.

This result indicated that the compound of the present invention was useful as a fluorescent substrate for detecting the enzymatic activity of a nitrile-related enzyme.

Example 3

Nitrilase-Catalyzed Reaction

1. Preparation of Crude Nitrilase Solution (Cell-Free Extract)

A recombinant *E. coli*, JM109/pSK002, which highly expresses *Rhodococcus* sp. strain SK92-derived nitrilase (JP 8-173169 A) was inoculated into 1 ml of a 50 ampicillin-containing LB medium (1% Bactotryptone, 0.5% Bactoyeast extract, 0.5% NaCl) and pre-cultured at 37° C. for 7 hours. The culture broth was taken in a volume of 0.1 ml and added to 100 ml of the same medium (containing 50 µg/ml ampicillin and 1 mM IPTG), followed by shaking culture at 37° C. for 15 hours. The resulting culture broth was centrifuged (3,700× g, 10 minutes, 4° C.) to collect the cells, which were then washed with 10 mM sodium phosphate buffer (pH 7.0) and suspended in the same buffer. As a control strain, JM109/pUC118 was used.

1 ml of the resulting cell suspension was homogenized for 1 minute under ice cooling with an ultrasonic homogenizer VP-15S (TAITEC Co., Ltd, Japan) under the following conditions: output control 4, DUTY CYCLE 40%, PULS, TIMER=B mode 10 s. The homogenate was then centrifuged (10,000×g, 5 minutes, 4° C.) and the resulting supernatant was collected as a cell-free extract.

2. Enzymatic Reaction

In the same manner as shown in Example 2, the reaction was performed using a nitrile fluorescent substrate (compound 2), followed by detection with a fluorescence imager.

Figure 4:
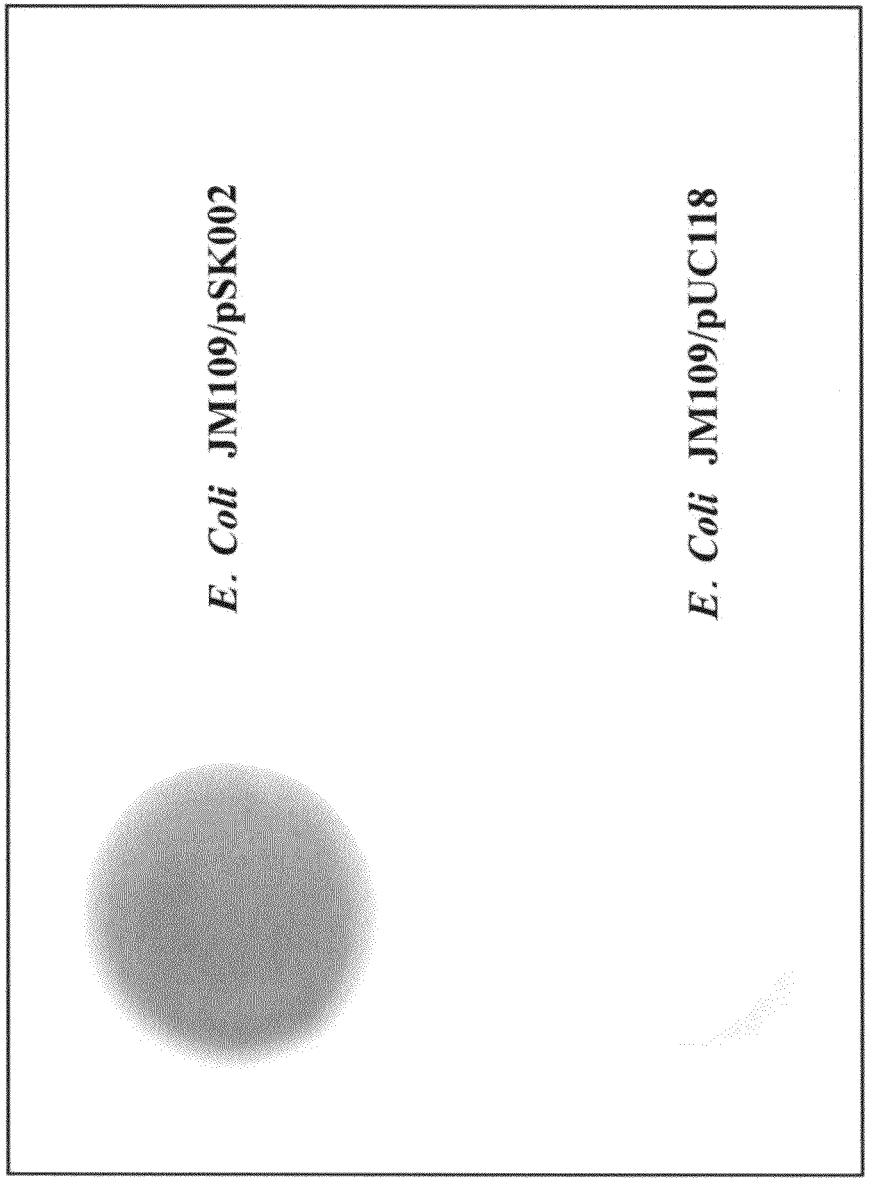
FIG. 4 shows the detection results of a nitrilase activity-induced increase in the fluorescence intensity of a fluorescent substrate.

The results obtained are shown in FIG. 4. The cell-free extract obtained from JM109/pUC118 used as a control sample showed no change in fluorescence, whereas there was a significant increase in the intensity of fluorescence when using the cell-free extract derived from the nitrilase-expressing recombinant.

This result indicated that the compound of the present invention was useful as a fluorescent substrate for detecting the enzymatic activity of a nitrile-related enzyme.

Example 4

Figure 5:
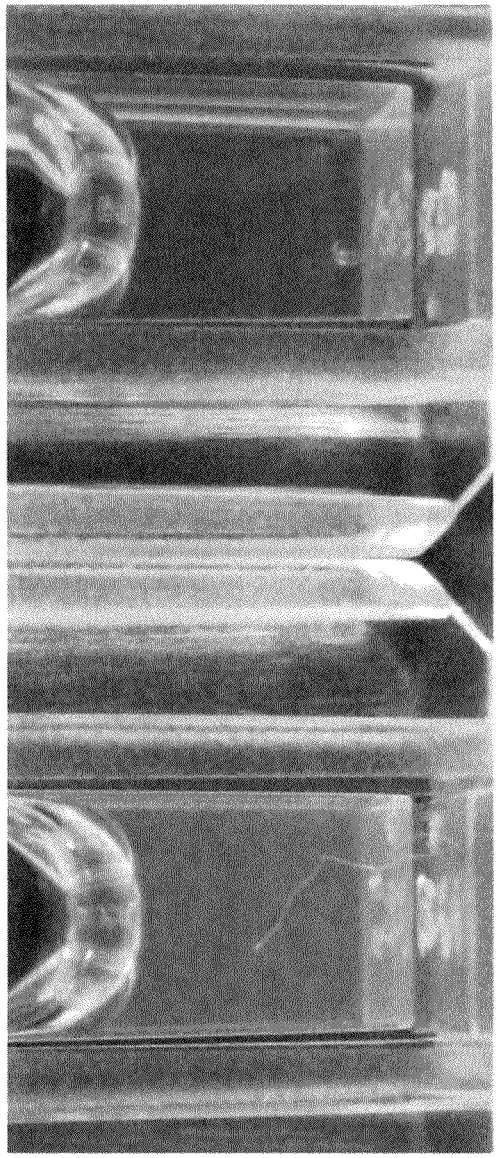
FIG. 5 shows the detection results of a nitrilase activity-induced increase in the fluorescence intensity of a fluorescent substrate.

10 µL of sodium phosphate buffer (pH 7.0), 75 µL of sterilized water and 5 µL of 0.1 mM nitrile fluorescent substrate (compound 2: dissolved in DMSO) were mixed together and pre-incubated at 30° C. A cell-free extract (10 µL), which had been prepared in the same manner as shown in Example 3, was added to initiate the reaction. After the reaction for 24 hours, the cell-free extract obtained from JM109/pUC118 used as a control sample showed little change in color, whereas significant green fluorescence was observed when using the cell-free extract derived from the nitrilase-expressing recombinant (FIG. 5).

This result indicated that the fluorescence intensity of the fluorescent substrate of the present invention was significantly high enough to be distinguishable by the naked eye from the control.

Example 5

Nitrile Hydratase-Catalyzed Reaction for Compound 7

1. Preparation of Crude Nitrile Hydratase Solution (Cell-Free Extract)

Nitrile hydratase solution was prepared in the same manner as shown in Example 2.

2. Detection of Nitrile Hydratase-Catalyzed Enzymatic Reaction Using Fluorometer 178 µL of sodium phosphate buffer (200 mM, pH 7.3) and 2 µL of 1 mM fluorescent substrate (compound 7 or compound 2: dissolved in DMSO) were mixed together and pre-incubated at 37° C. The cell-free extract prepared above (20 µL) was added to initiate the reaction. Sampling was conducted at one hour intervals by addition of 380 µL sodium phosphate buffer (200 mM, pH 7.3) to 20 µL reaction solution, and each sample was measured for its fluorescence using a spectrophotofluorometer, model F-4500 (Hitachi High-Technologies Corporation, Japan). The measurement was performed with 490 nm excitation light under the following conditions: a slit width of 2.5 nm/2.5 nm, a photomultiplier voltage of 700 V and 37° C.

Figure 7:
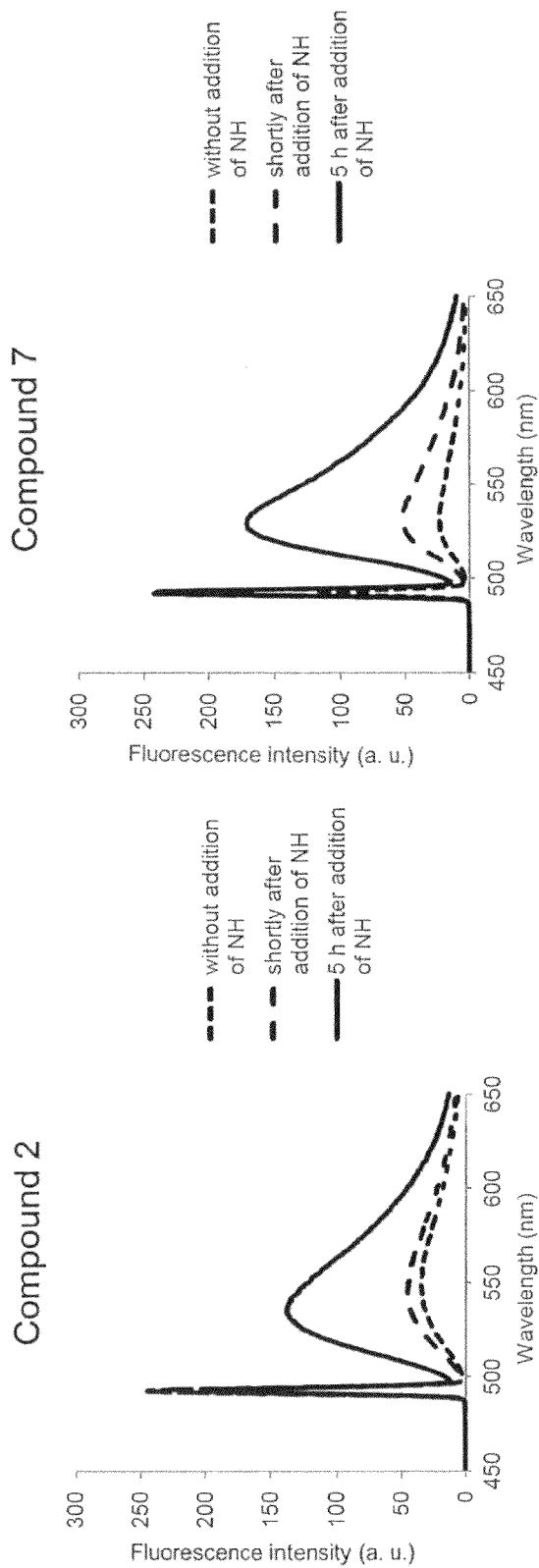
FIG. 7 shows nitrile hydratase-induced changes in fluorescence spectra.

As a result, compound 2 showed about a 3.9-fold increase in its fluorescence in comparison with a solution not containing the cell-free extract, whereas compound 7 showed about a 7.2-fold increase in its fluorescence in comparison with a solution not containing the cell-free extract (FIG. 7). Namely, the increase in fluorescence was shown to be 1.5-fold higher in compound 7 than in compound 2. In FIG. 7, it should be noted that "without addition of NH" represents the results obtained with the use of the above solution not containing the cell-free extract, "shortly after addition of NH" represents the results obtained immediately after addition of the cell-free extract, and "5 h after addition of NH" represents the results obtained at 5 hours after addition of the cell-free extract. It should be noted that "NH" denotes the cell-free extract (crude nitrile hydratase solution).

These results indicated that a fluorescent substrate comprising compound 7 allowed more sensitive detection of the enzymatic activity of a nitrile-related enzyme when compared to compound 2 which showed significantly high fluorescence intensity in Example 4.

3. HPLC Analysis on Nitrile Hydratase-Catalyzed Reaction Solution

Figure 8:
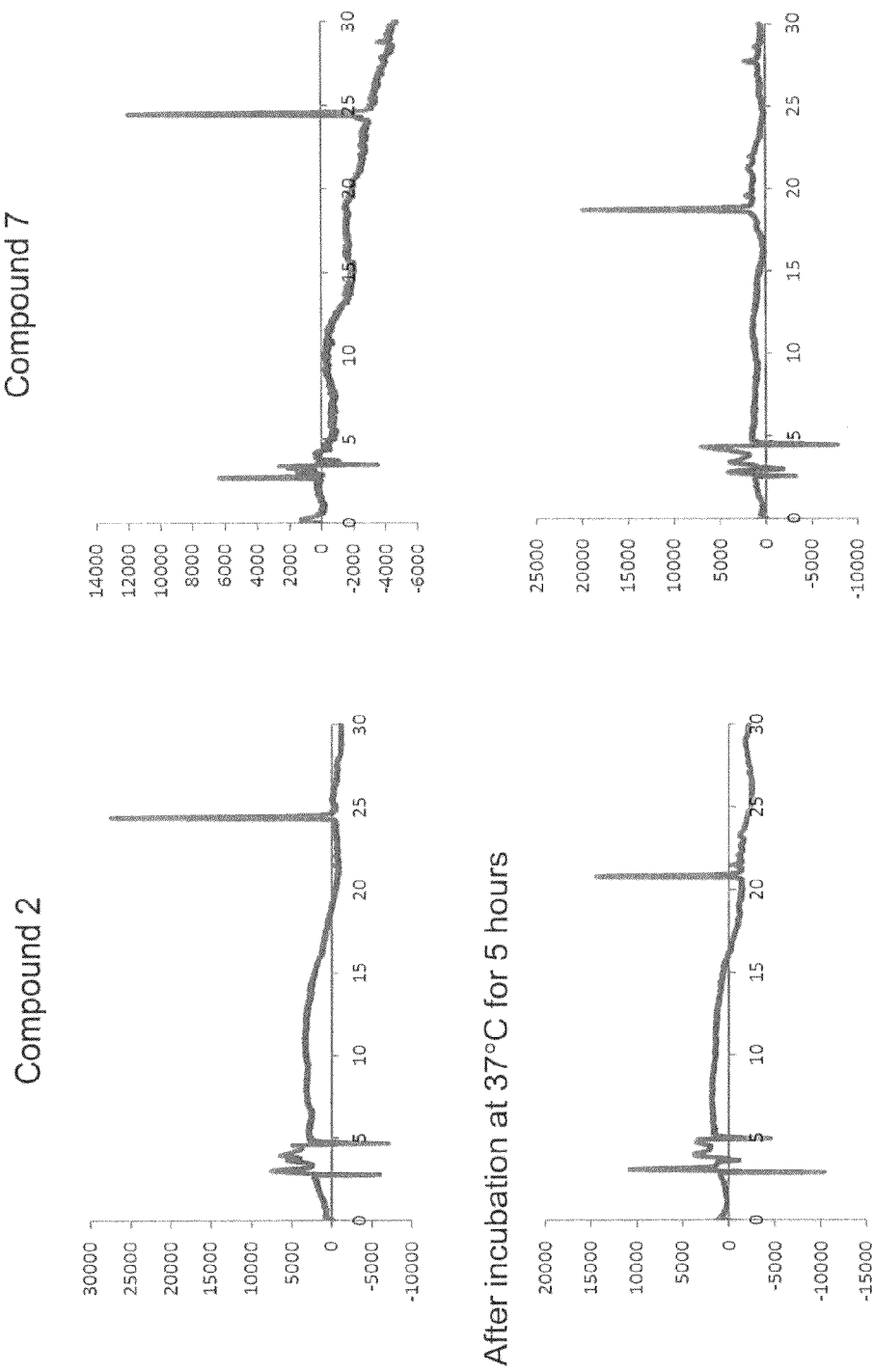
FIG. 8 shows the results of HPLC analysis on nitrile hydratase-catalyzed enzymatic reaction.

After reaction at 37° C. for 5 hours as described above, the reaction solution was analyzed by HPLC under the following conditions.
  Model: fluid delivery pump PU-2080 (JASCO)
  Column: Inertsil ODS-3 (4.6×250 mm) column (GL Sciences Inc.)
  Solvent: eluted with a linear gradient from 75% acetonitrile/0.1% TFA in water (0 min) to 15% acetonitrile/0.1% TFA in water (30 min)
  Detection: detector MD-2010 (JASCO), monitored by absorption at 500 nm As a result, the peak of compound 7 of the present invention disappeared, while a peak of a new product generated by the enzymatic reaction appeared (FIG. 8).

This result indicated the progress of the nitrile hydratase-catalyzed enzymatic reaction.

Example 6

Nitrilase-Catalyzed Reaction for Compound 7

1. Preparation of Crude Nitrilase Solution (Cell-Free Extract)
Nitrilase solution was prepared in the same manner as shown in Example 3.

2. Detection of Nitrilase-Catalyzed Enzymatic Reaction Using Fluorometer

Detection was conducted in accordance with the procedures shown in Example 5, provided that the compound used in the experiment was compound 7 and the enzyme solutions used were a cell-free extract derived from JM109/pSK002 (containing nitrilase) and a cell-free extract derived from the above control strain JM109/pTrc99A (having no nitrilase activity).

As a result, upon reaction with the JM109/pSK002-derived cell-free extract, compound 7 showed about a 7.5-fold increase in its fluorescence in comparison with the absence of the cell-free extract, whereas compound 7 reacted with the JM109/pTrc99A-derived cell-free extract showed little increase in its fluorescence.

Figure 9:
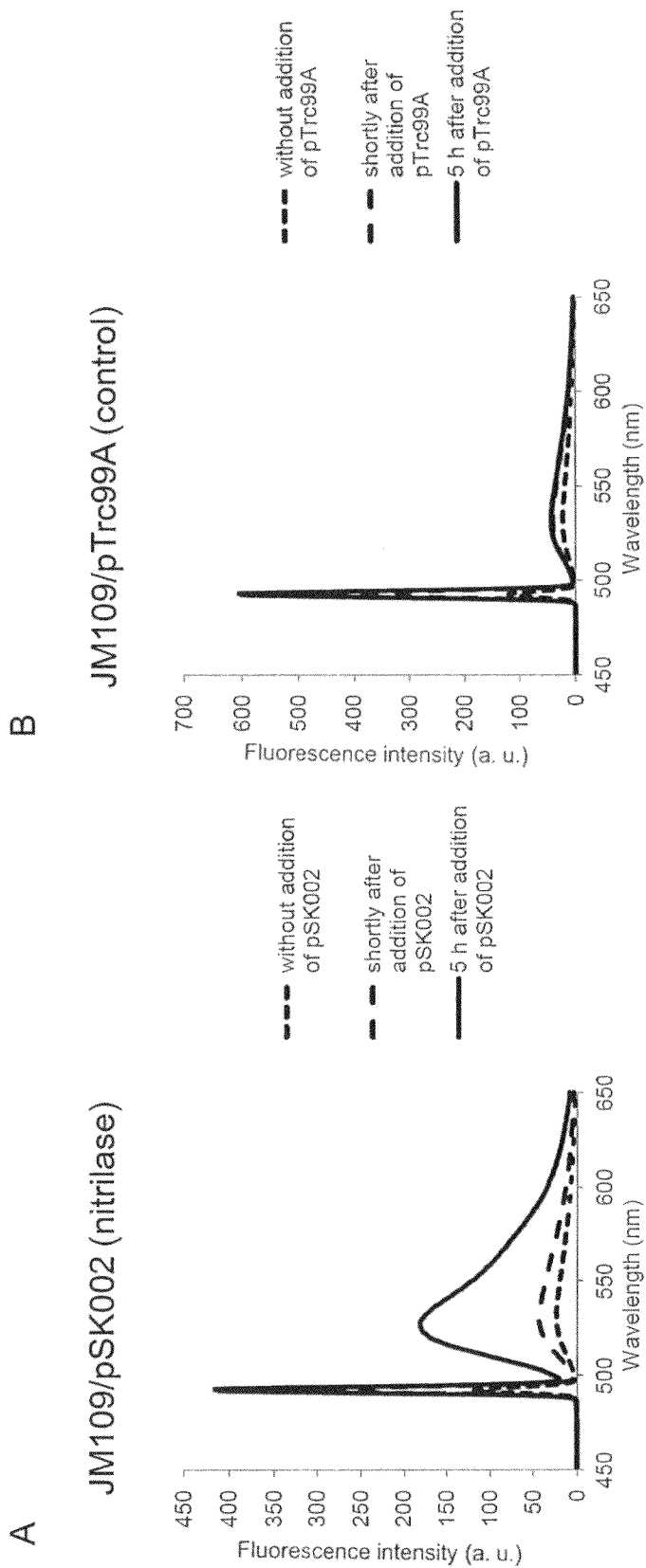
FIG. 9 shows nitrilase-induced changes in fluorescence spectra.

In FIG. 9A, it should be noted that "without addition of pSK002" represents the results obtained in the absence of the JM109/pSK002-derived cell-free extract, "shortly after addition of pSK002" represents the results obtained immediately after addition of the cell-free extract, and "5 h after addition of pSK002" represents the results obtained at 5 hours after addition of the cell-free extract.

Likewise, in FIG. 9B, "without addition of pTrc99A" represents the results obtained in the absence of the JM109/pTrc99A-derived cell-free extract, "shortly after addition of pTrc99A" represents the results obtained immediately after addition of the cell-free extract, and "5 h after addition of pTrc99A" represents the results obtained at 5 hours after addition of the cell-free extract.

3. HPLC Analysis on Nitrilase-Catalyzed Reaction Solution
Nitrilase activity was analyzed in accordance with the procedures shown in Example 4.

Figure 10:
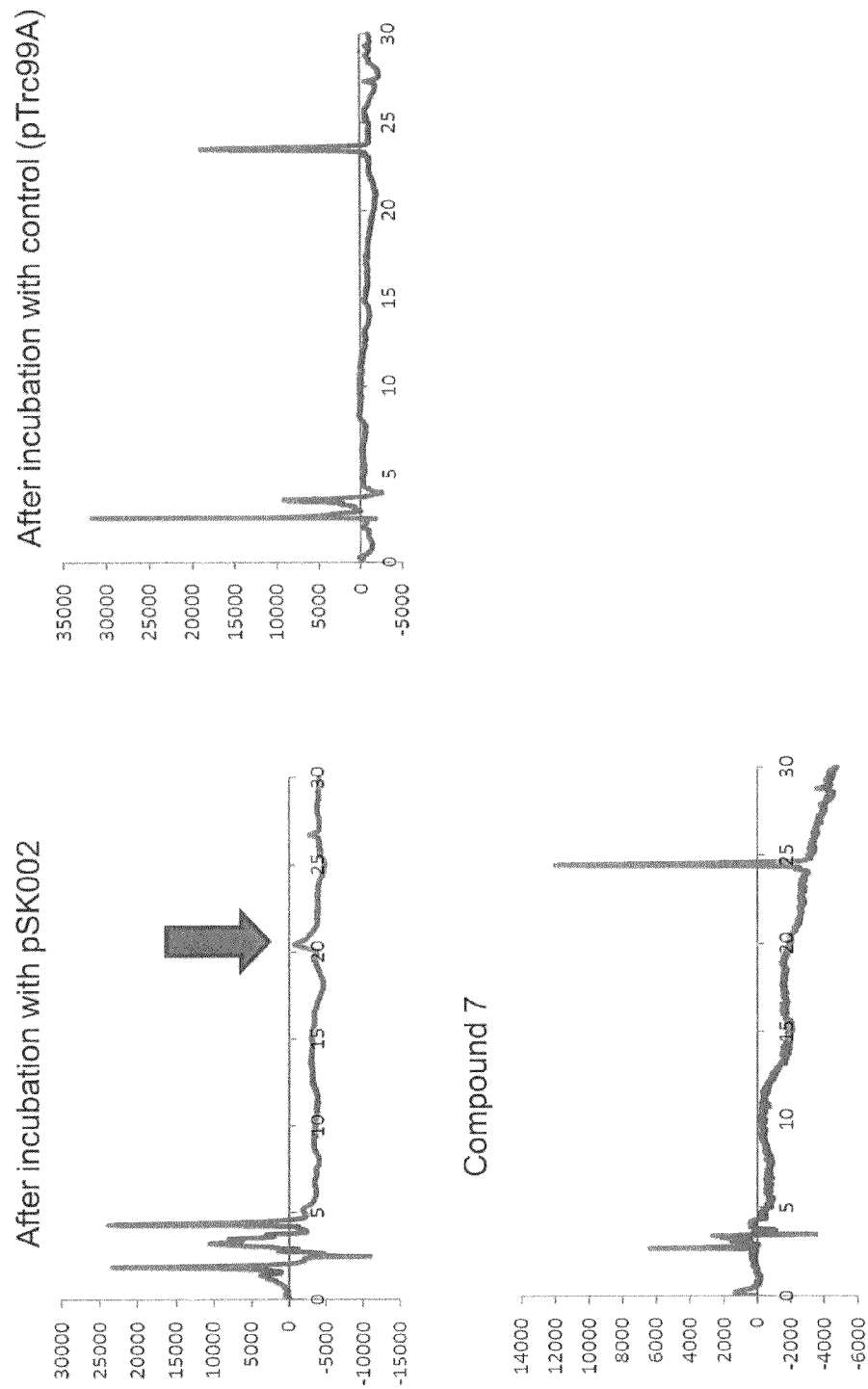
FIG. 10 shows the results of HPLC analysis on nitrilase-catalyzed enzymatic reaction.

As a result, the peak of compound 7 disappeared, while a peak of a new product generated by the enzymatic reaction appeared (FIG. 10). Namely, a reaction product was observed in the enzymatic reaction catalyzed by the JM109/pSK002-derived cell-free extract, whereas no reaction product was observed in the enzymatic reaction catalyzed by the JM109/pTrc99A-derived cell-free extract.

This result indicated the progress of the nitrilase-catalyzed enzymatic reaction for compound 7.

Example 7

Stability of Products

Product stability after enzymatic reaction was studied by HPLC analysis.

For HPLC analysis of the nitrile hydratase-catalyzed reaction solution (160 µL), the above pump, column, solvent conditions and detector were used to monitor absorption at 500 nm. On the other hand, for analysis of the nitrilase-catalyzed reaction solution (160 μL), the same procedure as used for analysis of the nitrile hydratase-catalyzed reaction solution was repeated to monitor absorption at 500 nm.

Figure 11:
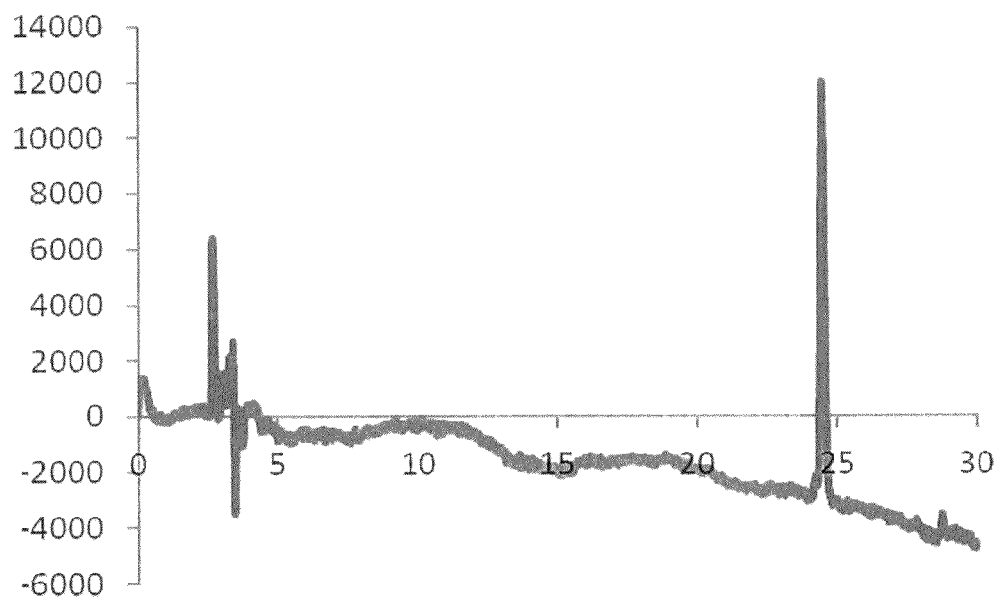
FIG. 11 shows the results of HPLC analysis on the stability of the product generated by nitrile hydratase-catalyzed enzymatic reaction.
Figure 11:
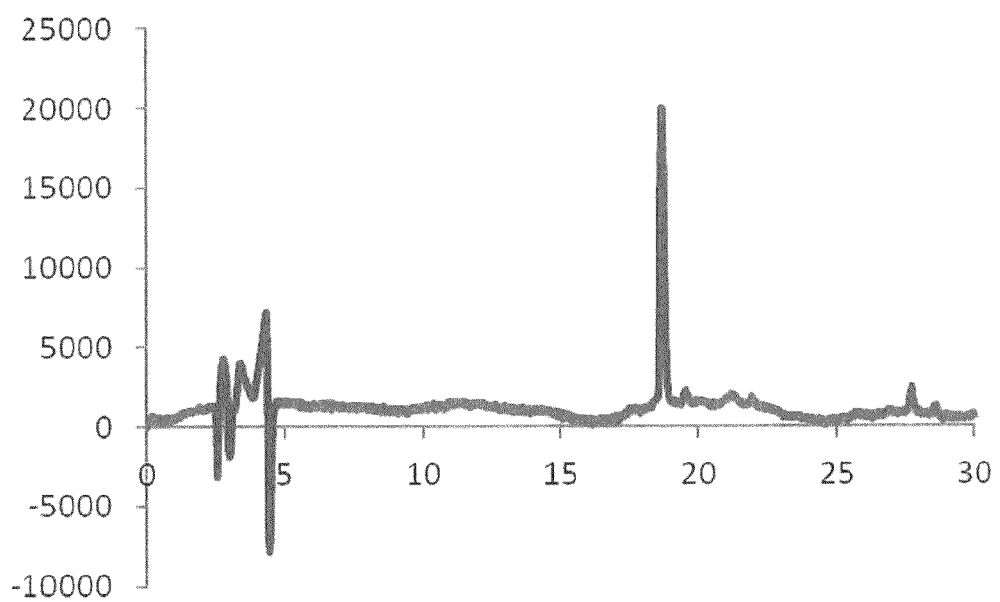

As a result, a peak corresponding to a product of the nitrile hydratase-catalyzed enzymatic reaction, i.e., 5-$CONH_2$ fluorescein 4-chlorobenzyl ester (compound 9) was observed, whereas any peak corresponding to its ester hydrolysis product 5-$CONH_2$ fluorescein was not observed (FIG. 11).

Figure 12:
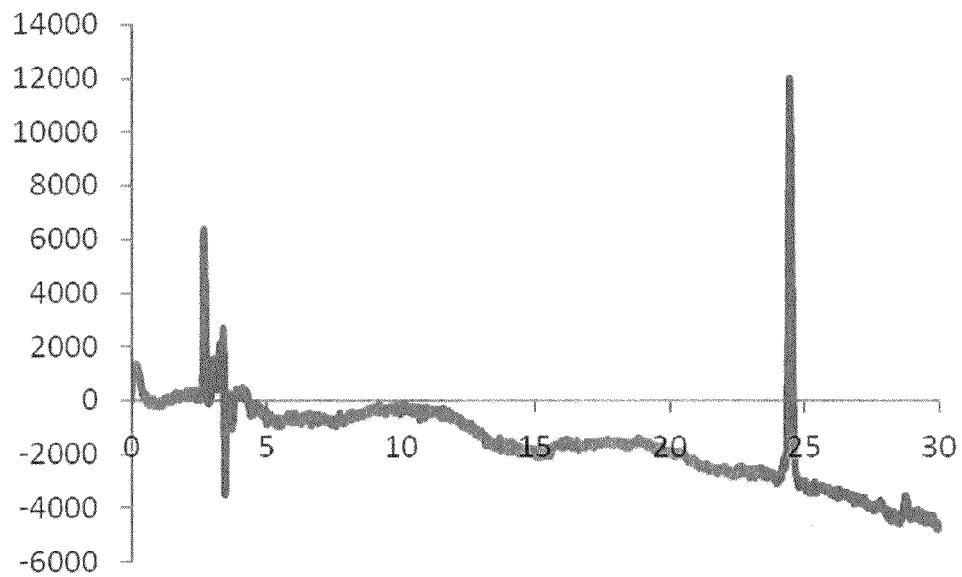
FIG. 12 shows the results of HPLC analysis on the stability of the product generated by nitrilase-catalyzed enzymatic reaction.
Figure 12:
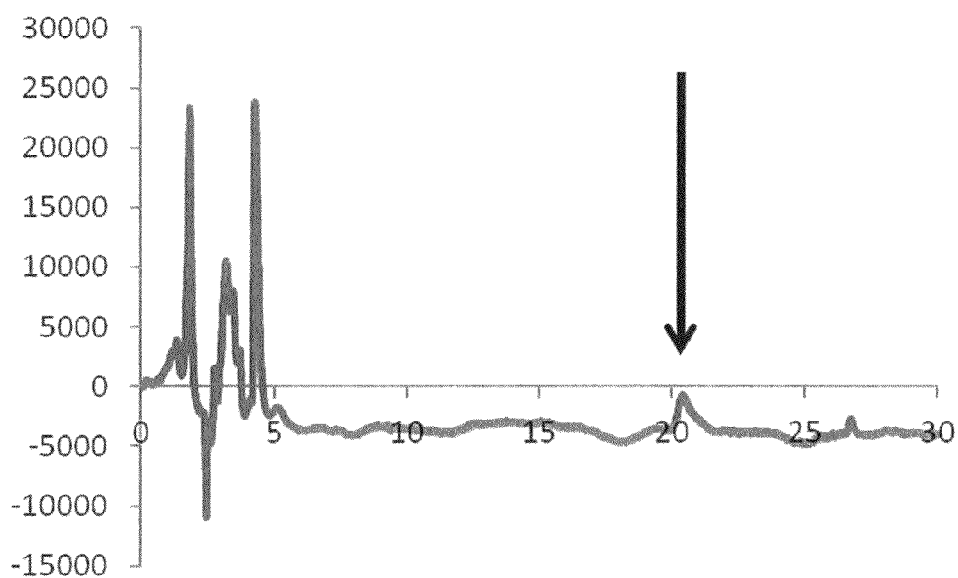

Likewise, a peak corresponding to a product of the nitrilase-catalyzed enzymatic reaction, i.e., 5-carboxylfluorescein 4-chlorobenzyl ester (compound 11) was observed, whereas any peak corresponding to its ester hydrolysis product 5-carboxylfluorescein was not observed (FIG. 12).

These results confirmed that the products would not substantially undergo ester hydrolysis in the enzyme solutions.

The foregoing results indicated that the fluorescent substrate of the present invention allows highly sensitive detection of the enzymatic activity of a nitrile-related enzyme.

INDUSTRIAL APPLICABILITY

The compound of the present invention allows fluorescence-mediated simple detection of enzymatic activity. Further, when combined with FACS or the like, the present invention enables the construction of a high-throughput system for enzymatic activity detection.

The invention claimed is:

1. A compound consisting of formula (I), a salt thereof, or a hydrate thereof:

wherein:
$R^1$ is —CN, —$CONH_2$, —CH=CH—CN, or —CH=CH—$CONH_2$;
$R^2$ is a halobenzyl group;
$R^3$, and $R^4$ are each independently a hydrogen atom, a halogen atom or a $C_{1-4}$ alkyl group; and
$R^5$ is a hydrogen atom, a $C_{1-4}$ alkylcarbonyl group, or a $C_{1-4}$ alkylcarbonyloxymethyl group.

2. A compound consisting of formula (II), a salt thereof, or a hydrate thereof:

3. A method for detecting nitrile-related enzymatic activity of a test substance, the method comprising:
(a) reacting the test substance with the compound of claim 1, a salt thereof or a hydrate thereof; and
(b) measuring optical intensity of an emitted wavelength generated-as a result of the reacting,
wherein an increase in the measured optical intensity compared to the compound without reacting to the test substance is indicative of nitrile-related enzymatic activity.

4. The method of claim 3, wherein the nitrile-related enzymatic activity is an activity of one enzyme selected from the group consisting of nitrilase, nitrile hydratase, and amidase.

5. The method of claim 3, wherein:
$R^1$ is —CN or —CH=CH—CN; and
the enzymatic activity is the activity of nitrilase or nitrile hydratase.

6. The method of claim 3, wherein:
$R^1$ is —$CONH_2$ or —CH=CH—$CONH_2$; and
the enzymatic activity is the activity of amidase.

7. The method of claim 3, wherein the measuring comprises flow cytometry.

8. A fluorescent substrate comprising the compound of claim 1, a salt thereof, or a hydrate thereof, wherein the substrate is suitable for detecting an enzymatic activity of a nitrile-related enzyme.

9. The substrate of claim 8, wherein the nitrile-related enzyme is a member selected from the group consisting of nitrilase, nitrile hydratase, and amidase.

10. The substrate of claim 8, wherein:
$R^1$ is —CN or —CH=CH—CN; and
the nitrile-related enzyme is nitrilase or nitrile hydratase.

11. The substrate of claim 8, wherein:
$R^1$ is —$CONH_2$ or —CH=CH—$CONH_2$; and
the nitrile-related enzyme is amidase.

12. A kit, comprising the compound of claim 1.

13. The kit of claim 12, further comprising a cell lysis solution, a buffer and instructions.

14. A method for detecting nitrile-related enzymatic activity of a test substance, the method comprising:
(a) reacting the test substance with the compound of claim 2, a salt thereof or a hydrate thereof; and
(b) measuring optical intensity of an emitted wavelength generated-as a result of the reacting,
wherein an increase in the measured optical intensity compared to the compound without reacting to the test substance is indicative of nitrile-related enzymatic activity.

15. A fluorescent substrate comprising the compound of claim 2, a salt thereof, or a hydrate thereof, wherein the substrate is suitable for detecting an enzymatic activity of a nitrile-related enzyme.

16. A kit, comprising the compound of claim 2.

17. The kit of claim 16, further comprising a cell lysis solution, a buffer, or a combination thereof and instructions.

* * * * *